United States Patent [19]

Schiff

[11] 4,175,264
[45] Nov. 20, 1979

[54] ELECTRONIC SYNCHRONIZER-MONITOR SYSTEM FOR CONTROLLING THE TIMING OF MECHANICAL ASSISTANCE AND PACING OF THE HEART

[76] Inventor: Peter Schiff, Box 117, Schwenksville, Pa. 19473

[21] Appl. No.: 759,874

[22] Filed: Jan. 17, 1977

Related U.S. Application Data

[62] Division of Ser. No. 556,153, Mar. 6, 1975, Pat. No. 4,016,871.

[51] Int. Cl.$^2$ ............................................. G06K 15/20
[52] U.S. Cl. .................................. 340/747; 128/1 D; 340/800
[58] Field of Search ................... 340/324 A, 324 AD; 128/2.06 R

[56] References Cited

U.S. PATENT DOCUMENTS

| | | | |
|---|---|---|---|
| 3,406,387 | 10/1968 | Werme | 340/324 A |
| 3,585,440 | 6/1971 | Lee et al. | 340/324 AD |
| 3,752,917 | 8/1973 | Foley et al. | 340/324 AD |
| 3,978,470 | 8/1976 | McGuire | 340/324 AD |

*Primary Examiner*—David L. Trafton
*Attorney, Agent, or Firm*—Lerner, David, Littenberg & Samuel

[57] ABSTRACT

A system which is capable of simultaneously displaying a plurality of waveforms on the face of a CRT which are representative of ECG, arterial pressures and operating states of the mechanical heart assistance devices, as well as a "timing bar" which sweeps across the CRT face in synchronism with the ECG trace, for example.

Optical pickups are slidably mounted adjacent the CRT face across the path of the "timing bar" sweep for activating photodetectors which in turn initiate inflation and deflation of mechanical assistive devices at any desired point along the ECG or pressure trace. Any one of the pressure or ECG traces may be "frozen" on the display face to facilitate comparison between a trace of the condition of the heart prior to the use of heart assistance and a trace of the augmented condition. All traces may be freely moved to any location upon the display face so as to permit close positioning and even superimposition of two or more traces to still further facilitate visual comparisons. The "timing bar" may also be utilized to provide an electrical pacing assist for controlling patient heart rate as well as for extending the heart refractory period enabling the assistance devices to operate at reduced rates. Means are provided for presenting "frozen" and regular traces at different display intensities.

17 Claims, 17 Drawing Figures

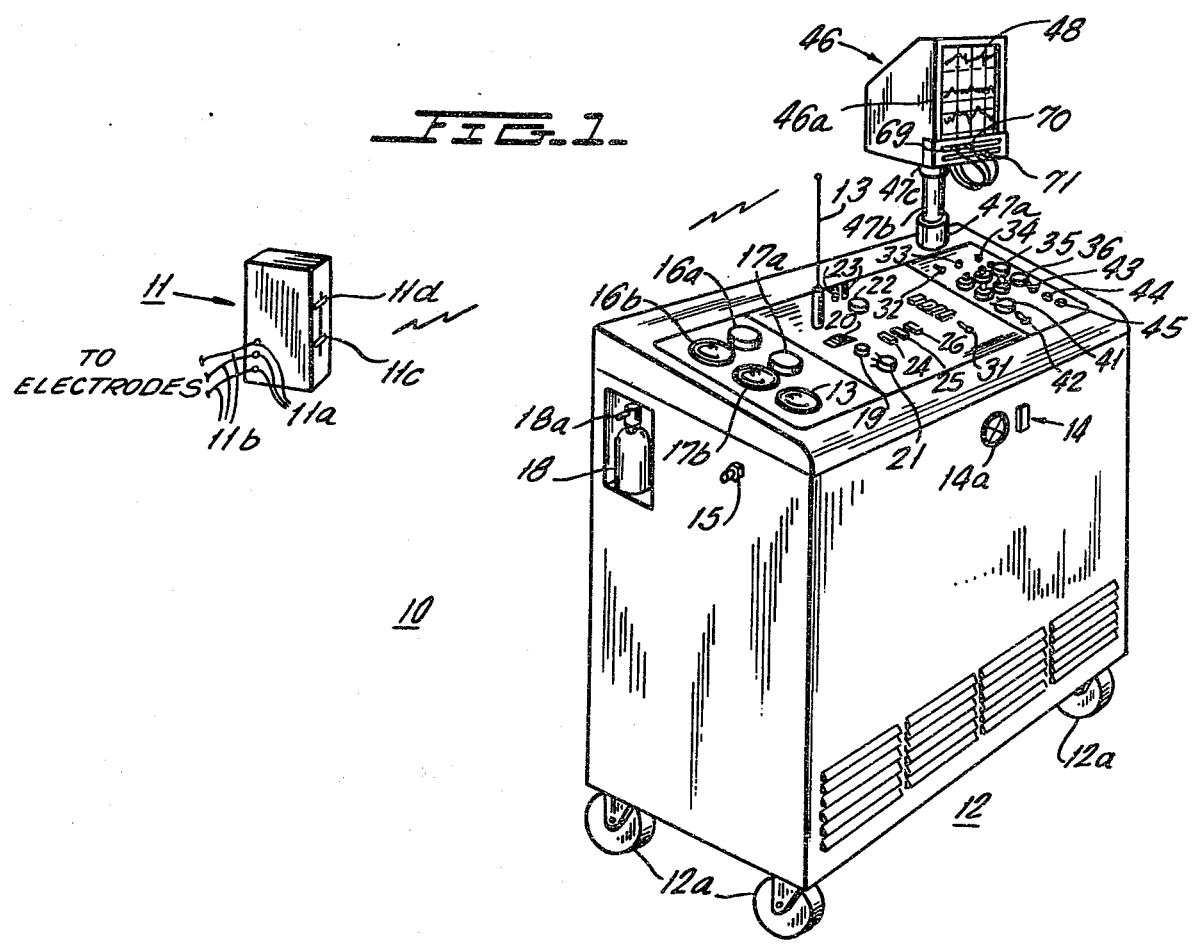

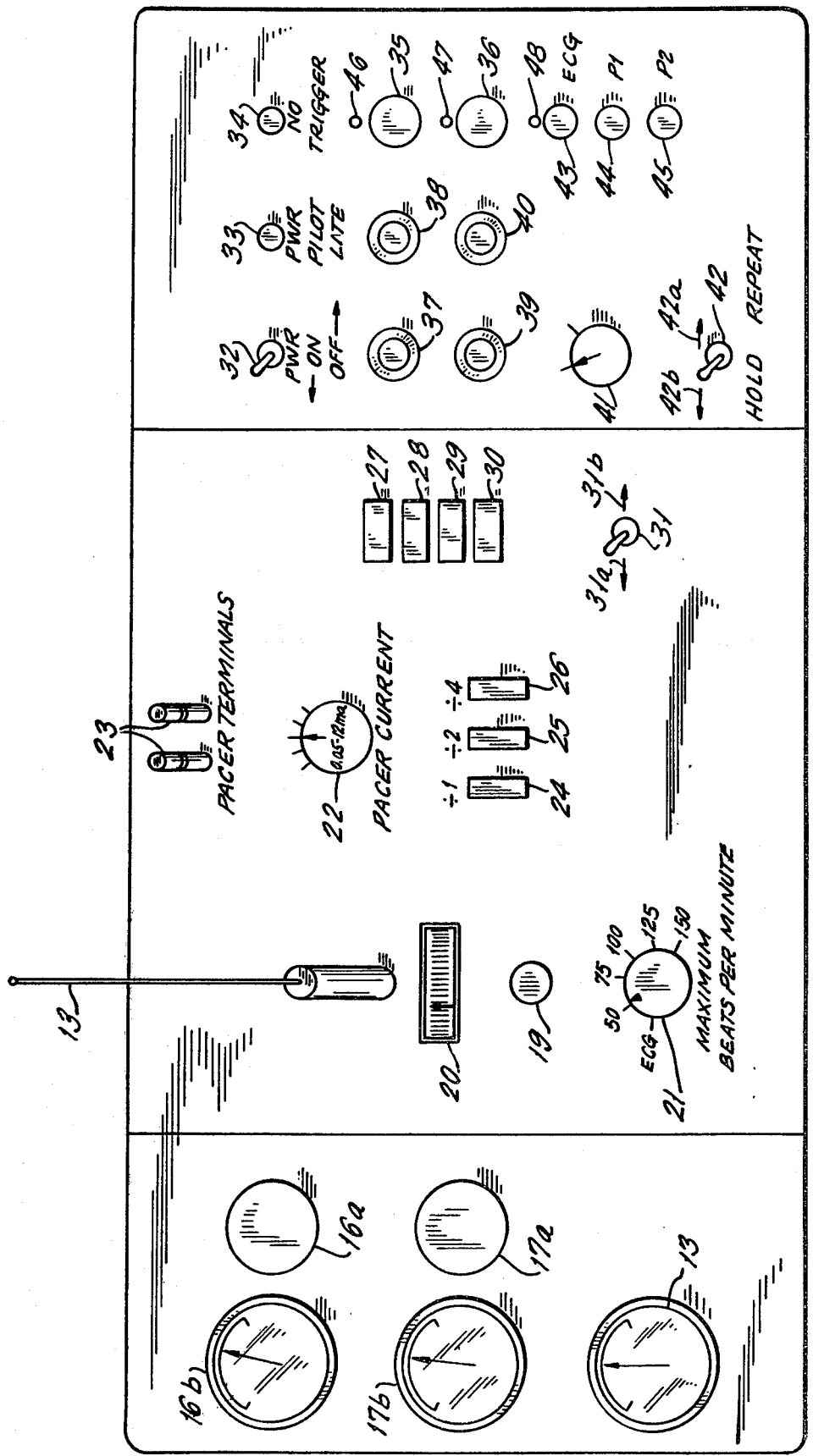

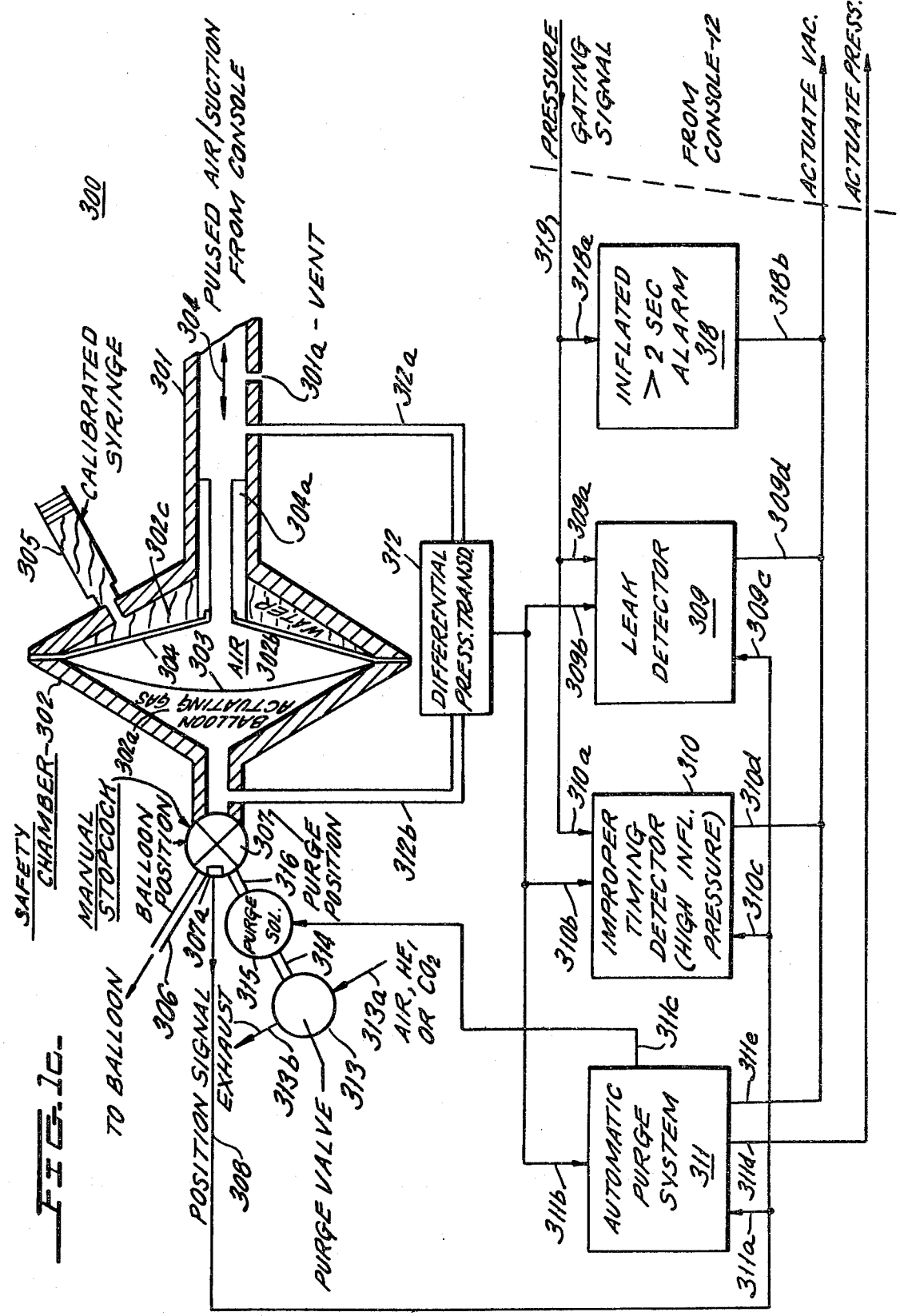

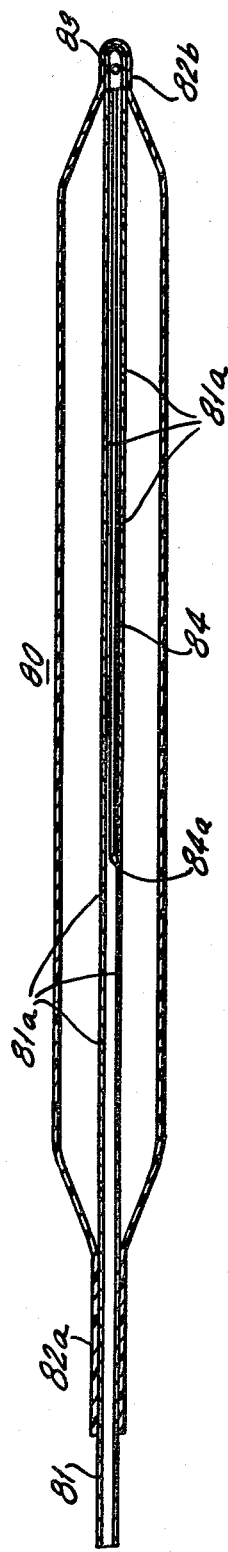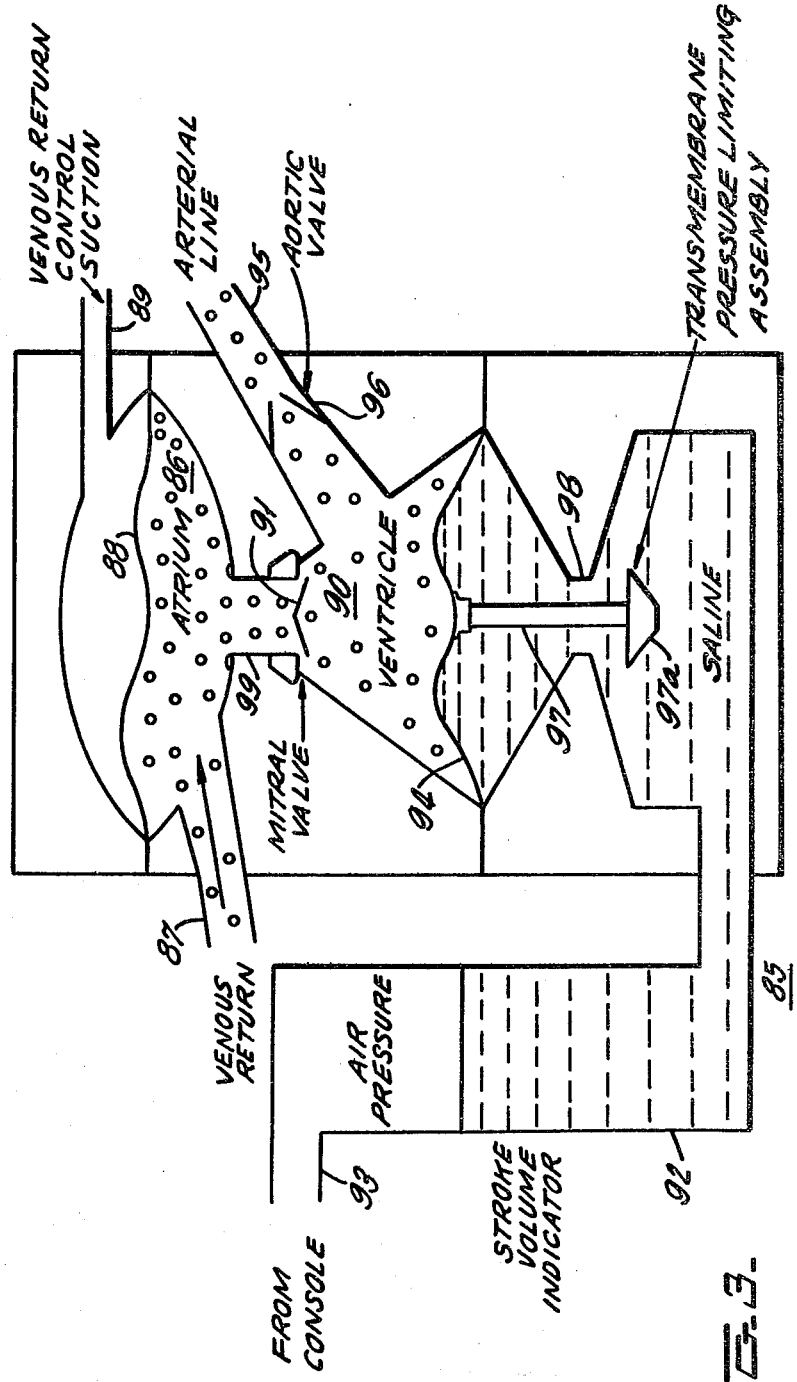

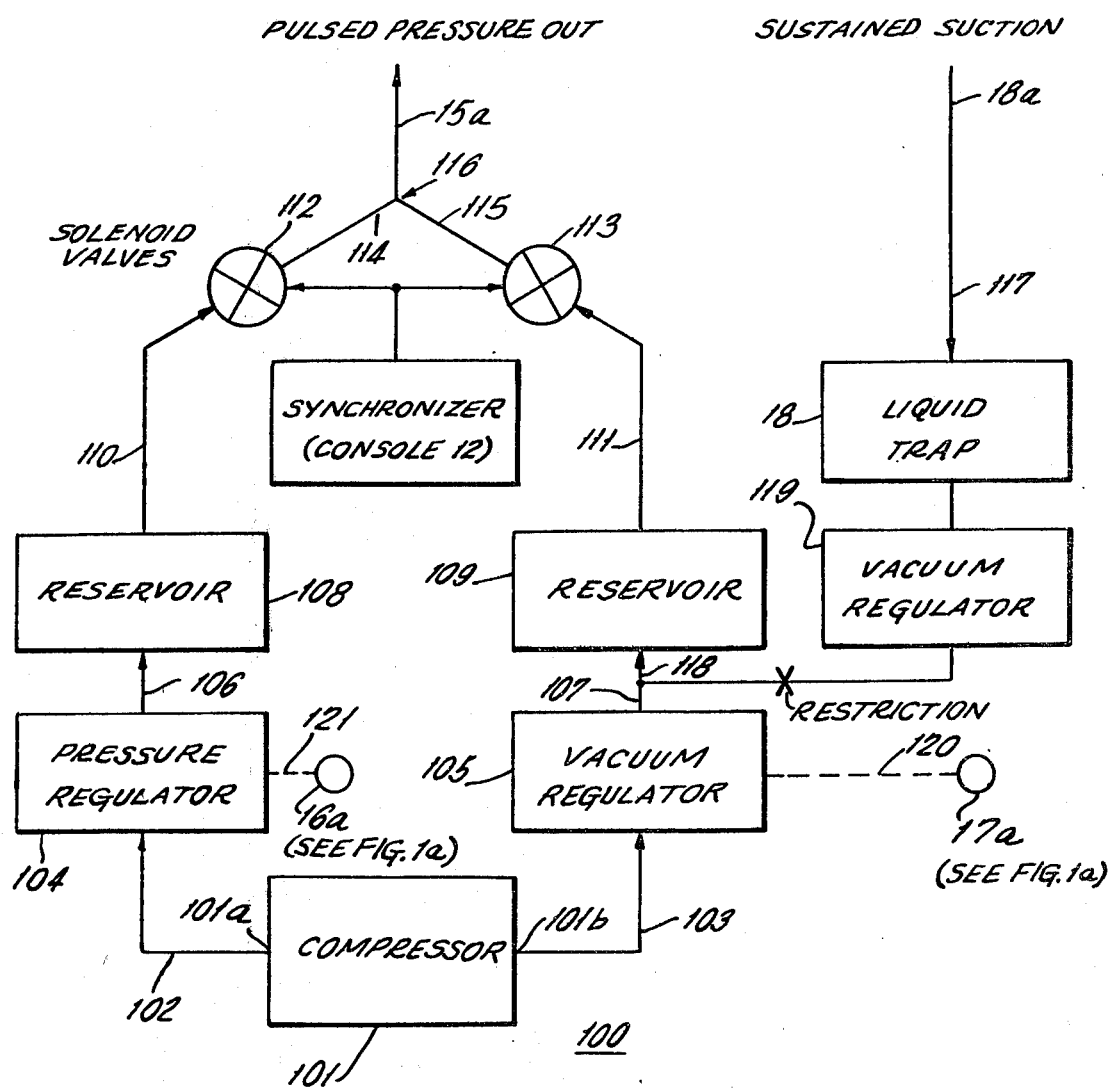

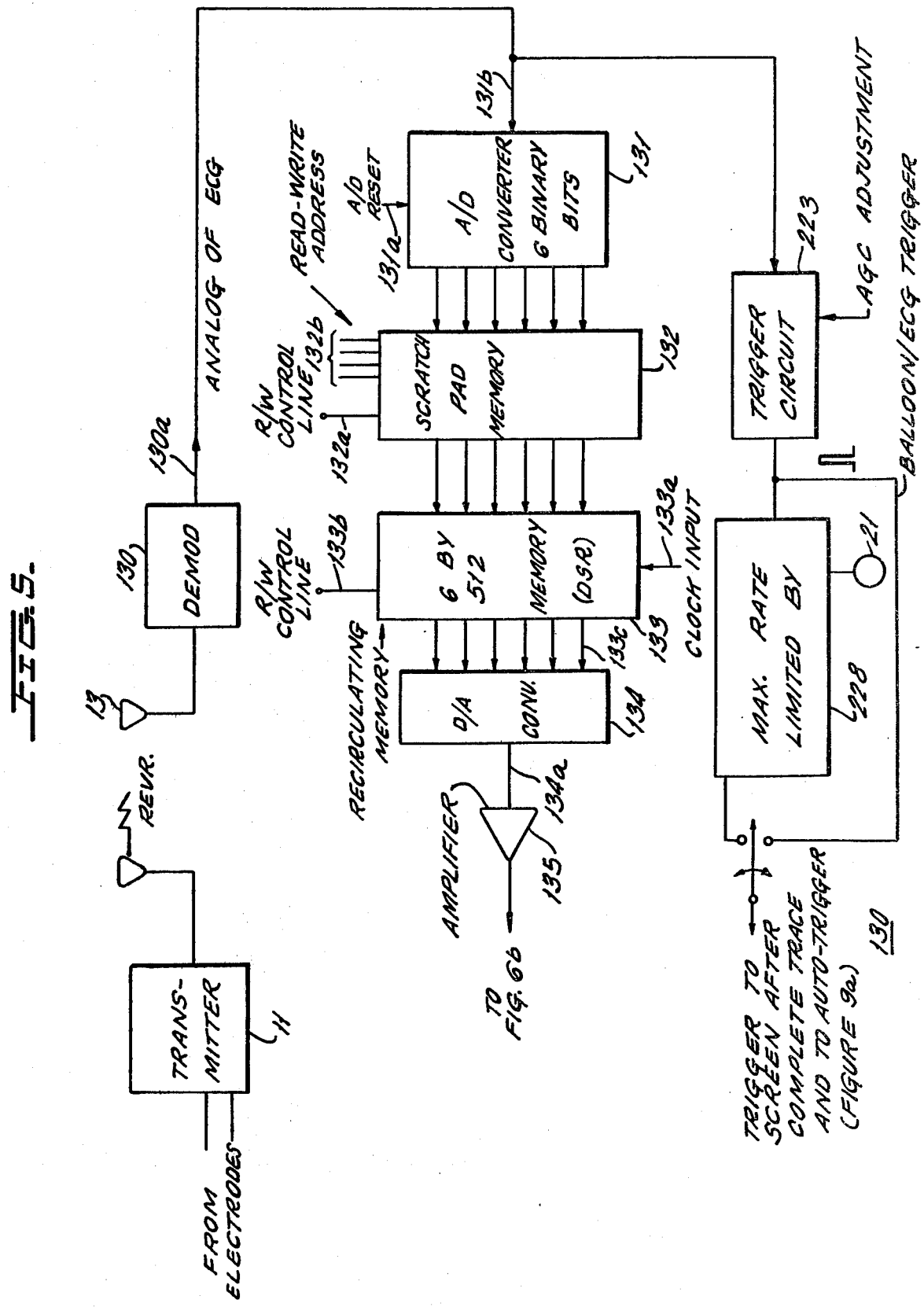

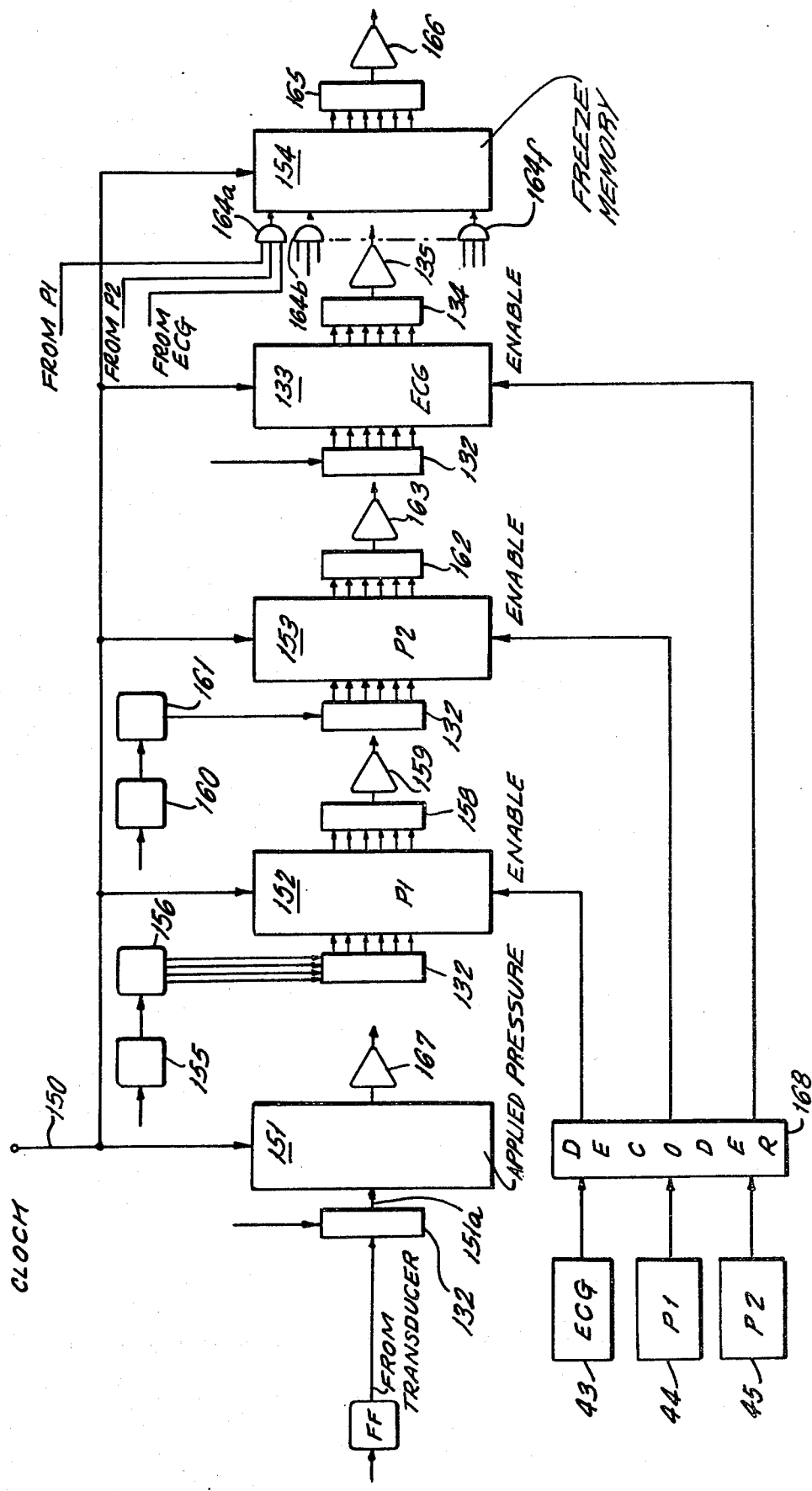

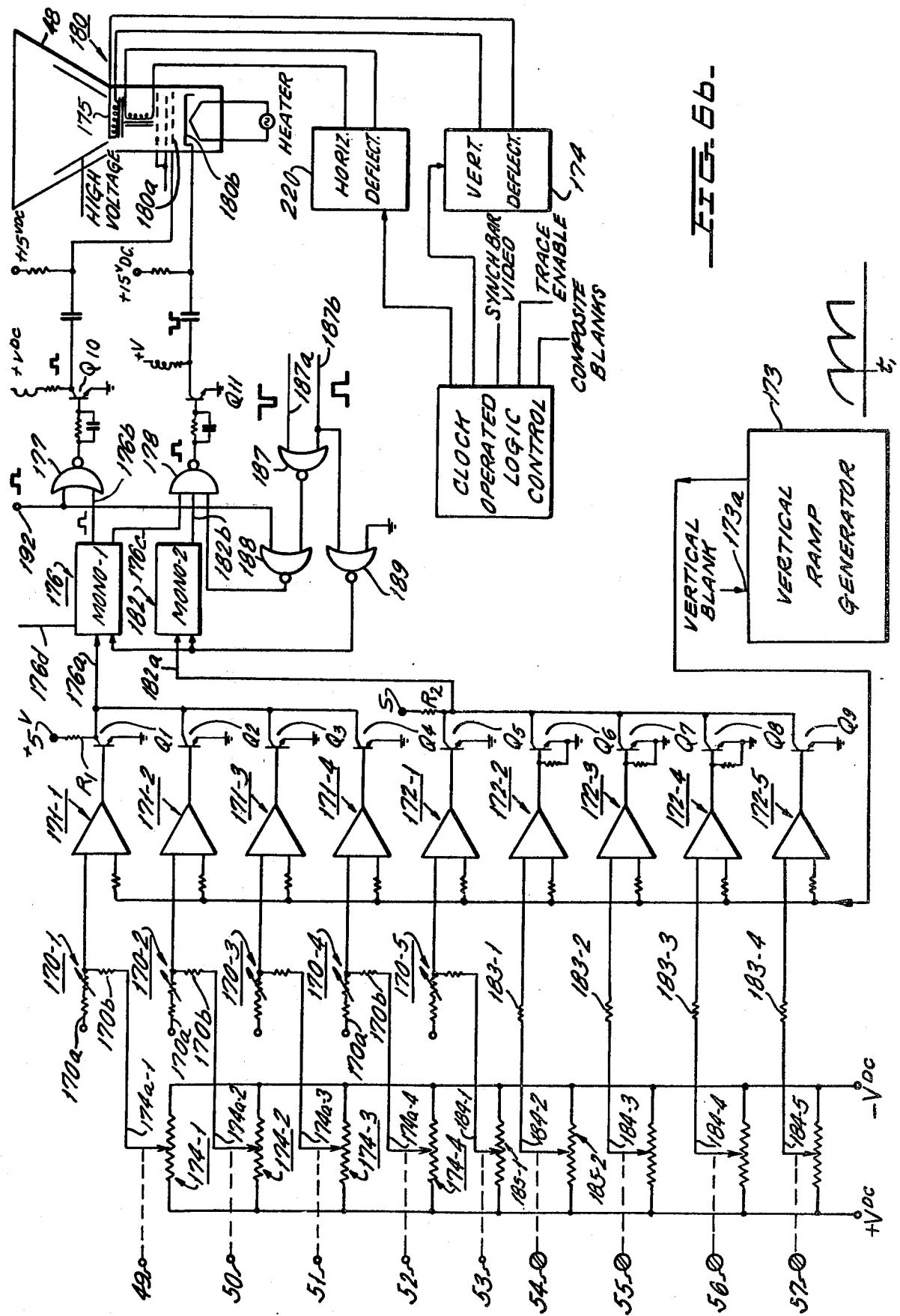

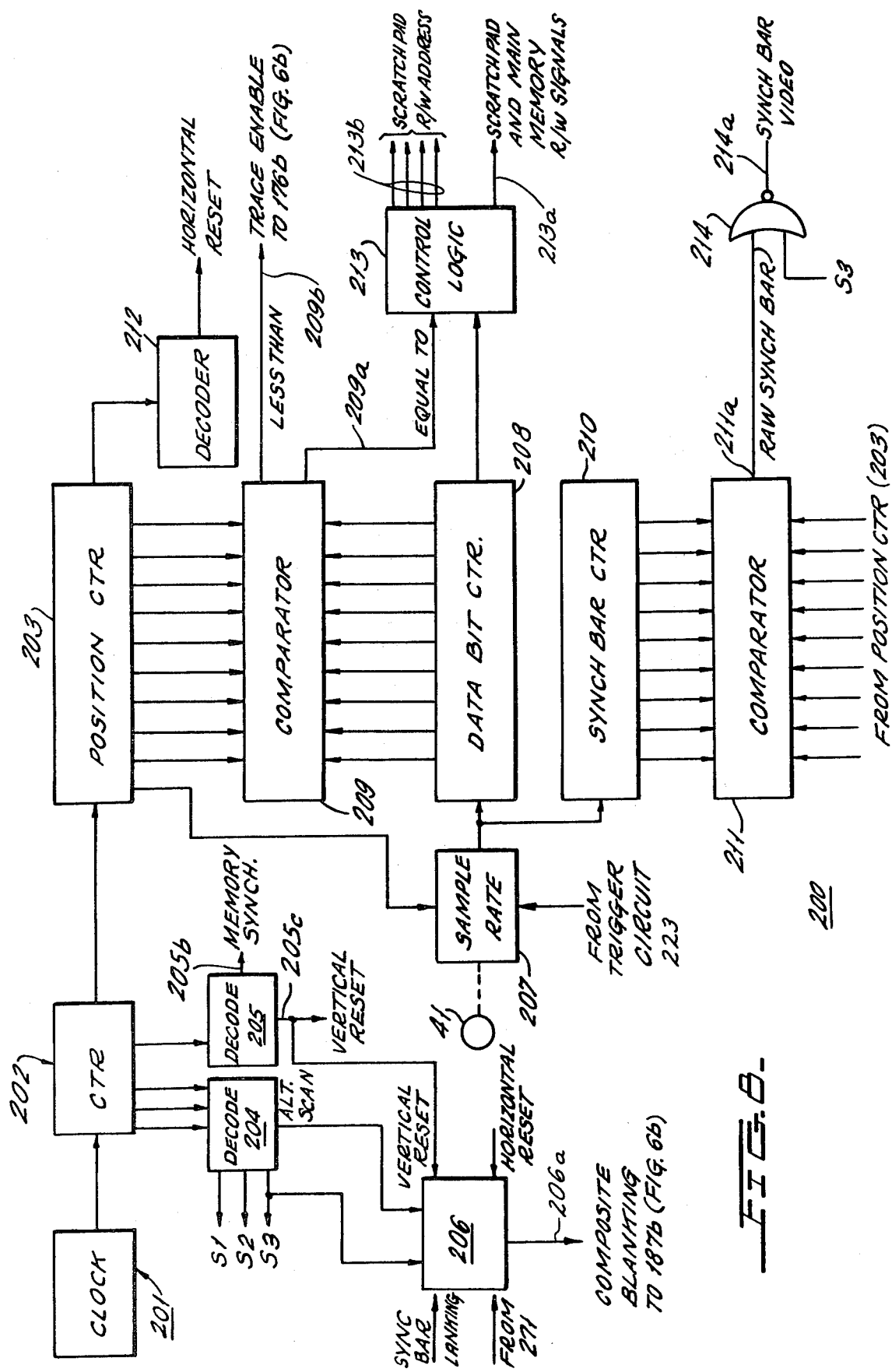

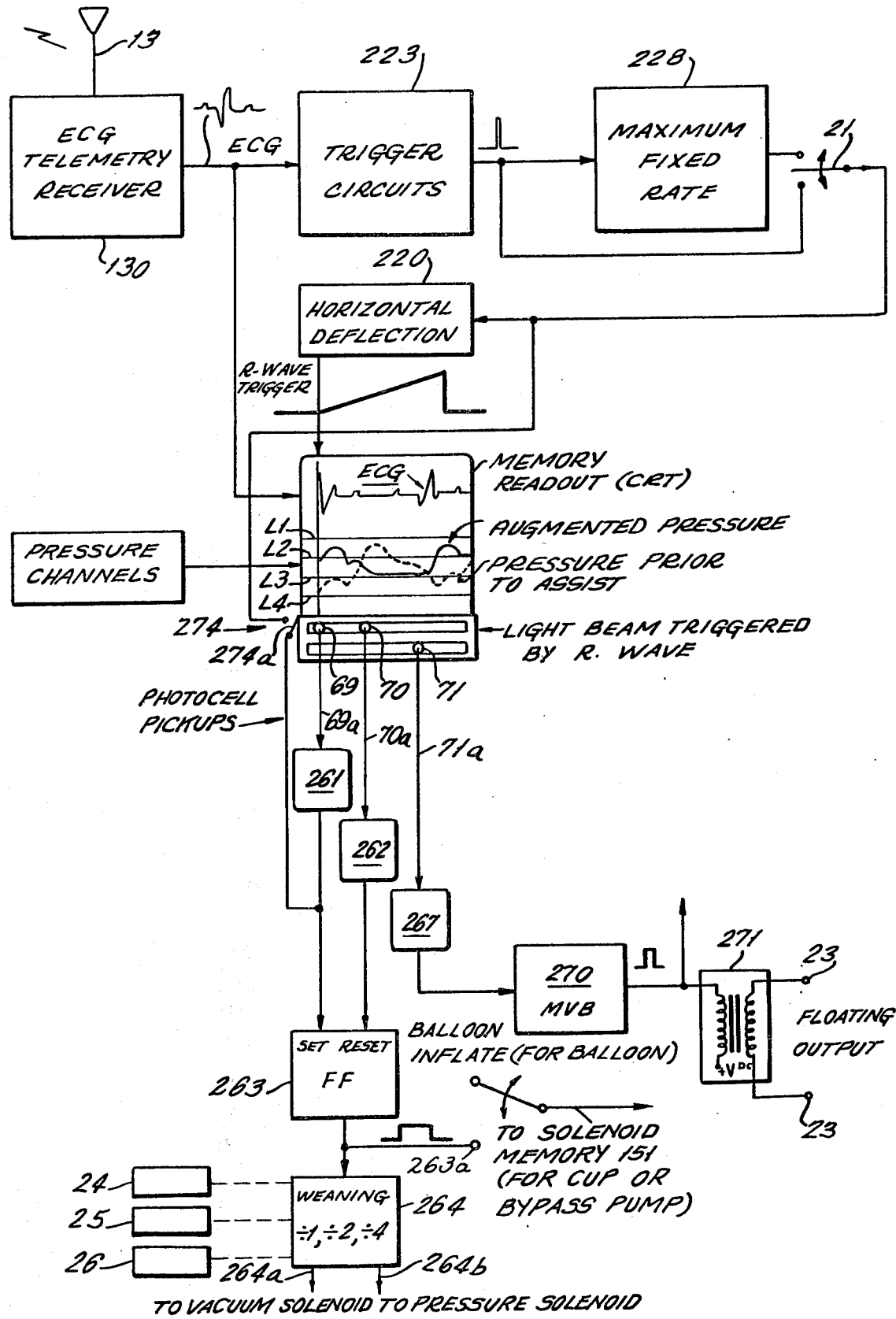

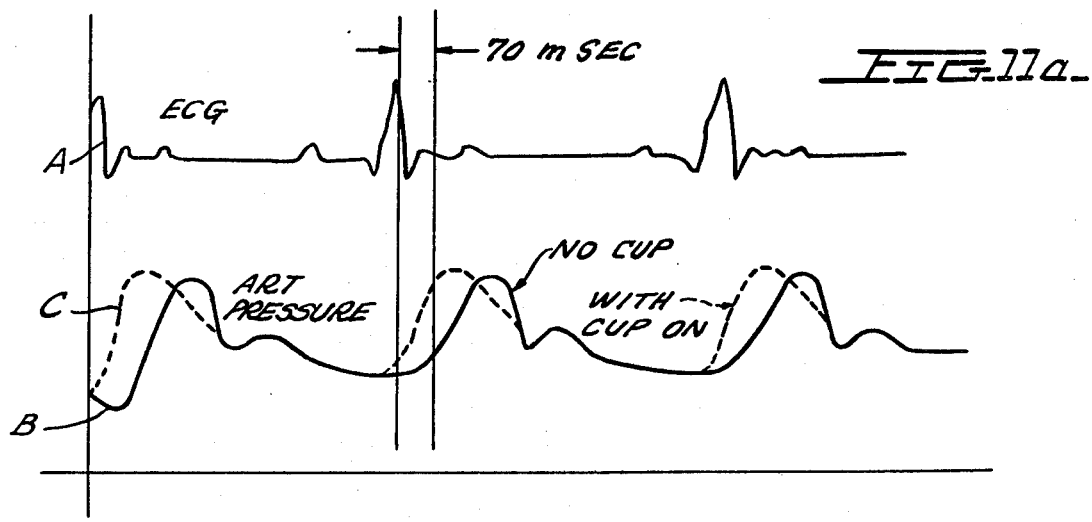
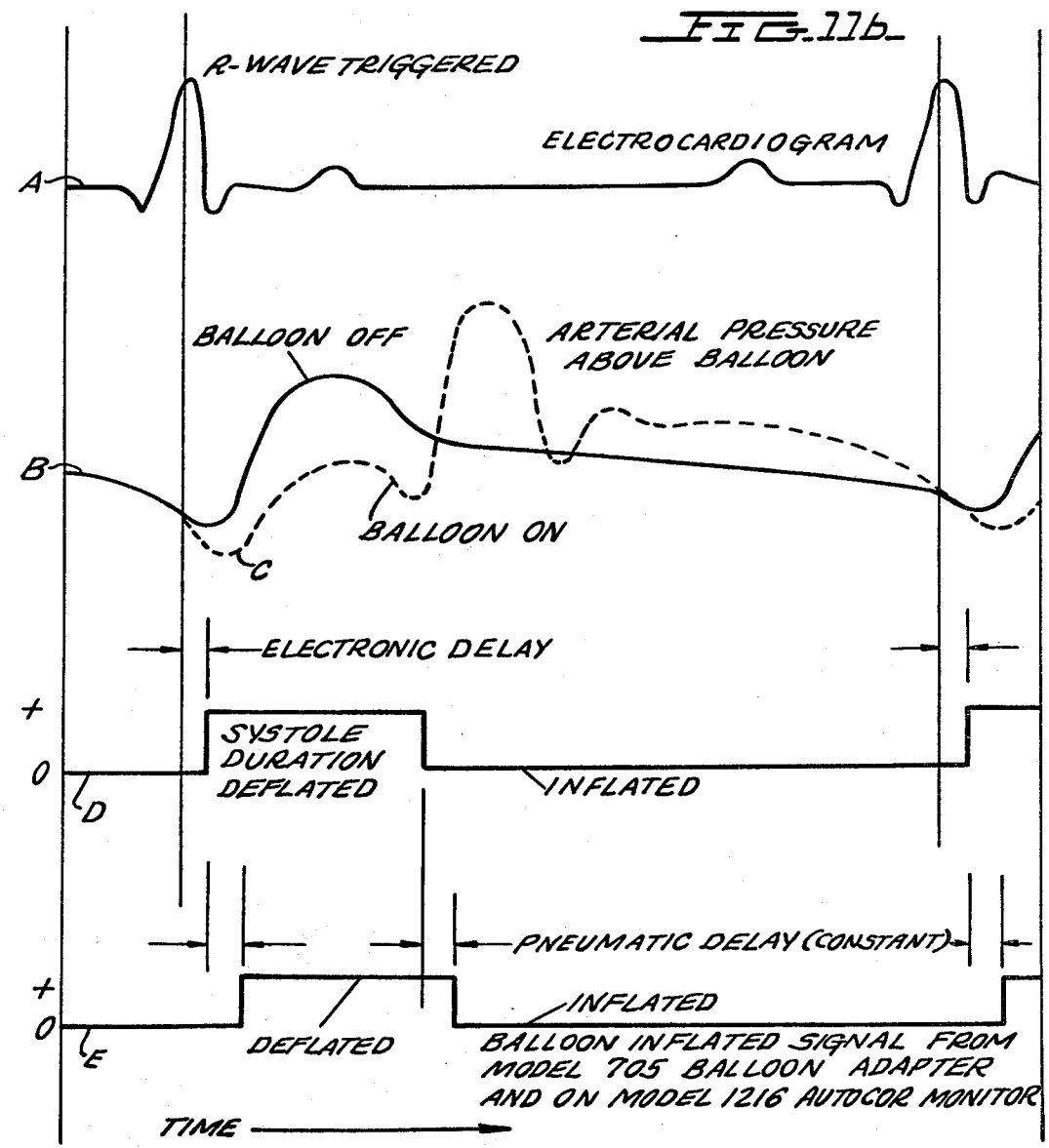

ELECTRONIC SYNCHRONIZER-MONITOR SYSTEM FOR CONTROLLING THE TIMING OF MECHANICAL ASSISTANCE AND PACING OF THE HEART

This is a Division of application Ser. No. 556,153, filed Mar. 6, 1975, now U.S. Pat. No. 4,016,871.

BACKGROUND OF THE INVENTION

The present invention relates to devices for monitoring and controlling the operation of a human or animal heart and more particularly to a novel monitor and control system which provides for activation of mechanical or electrical assistance devices directly from the display screen thereby eliminating a human interface which is required in present day systems.

Significant technological advancements have been made in the treatment of heart patients in recent years. It is now possible, through the use of devices such as pacemakers, mechanical ventricular assistance devices, bypass pumps and intra-aortic balloon pumps to improve prognosis in severely ill cardiac patients. Mechanical ventricular assistance is provided, for example, by a device commonly known as the Anstadt cup which fits about the ventricles of the heart and which provides full circulatory support for resuscitation or preservation of the organs, mechanical systole and mechanical diastole being provided by alternating pulsed positive and negative pressures applied to the cup. Intra-aortic balloons are typically inserted into the descending aorta and are normally inflated during diastole and deflated during systole to decrease left ventricular pressure and hence the resultant activity of the heart. Immediately after left ventricular rejection the balloon is again inflated to raise diastolic pressures and increase coronary perfusion thereby mechanically assisting and augmenting the pumping action of the heart to significantly enhance recovery of the patient.

Pacemakers are typically utilized to restore a regular heartbeat while pulsatile bypass pumps, which are essentially a model of the left-side of the heart and are provided with an atrium and ventricle, are utilized to provide diastolic or systolic augmentation or total body perfusion during heart surgery.

All of the above mechanical or electrical assist devices require that trained personnel continuously observe displays of ECG traces and arterial pressure readings and, based upon these human observations, the trained personnel must then adjust control knobs and the like to provide for appropriate control of the mechanical assistive devices so as to appropriately synchronize their operation with the patient's heart. This "human" interface is extremely demanding, even upon trained personnel, making it extremely difficult to exert proper control over the mechanical or electrical assist devices and making it effectively impossible to cause such mechanical or electrical assistive devices to substantially instantaneously respond to the continuously changing displayed information.

BRIEF DESCRIPTION OF THE INVENTION

The present invention is characterized by providing novel monitor and control equipment for use with mechanical and electrical assistive devices of the type described, wherein the "human" interface required with present day equipment is substantially eliminated.

The monitor and control equipment of the present invention incorporates a circulatory assist system capable of actuating the Anstadt cup for direct mechanical ventricular assistance, or the intra-aortic balloon pump or a bypass pump. The system incorporates a unique monitor scope having an electronic memory capable of simultaneously displaying an electrocardiogram, two pressure traces and an assist transducer inflation trace, all of which are displayed in their entirety or which may be "frozen" at will for insepection or comparison purposes. In addition, a previous or "prior to augmentation" trace may be retained in a memory to assure optimal assist timing by allowing direct comparison of the augmented versus the non-augmented ECG or pressure traces. The sweep rate of the monitor scope is triggered by the electrocardiogram so that the same portion of the cardiac cycle appears on the same part of the CRT display face in subsequent sweeps. Systolic and diastolic control signals as well as pacing signals are derived directly from the CRT display face which generates a "timing bar" which sweeps the display face at the sweep rate of the ECG trace. Triggering pulses are generated by photosensitive devices coupled to optical pickups through fiber optic bundles, the pickups being slidably mounted along the sweep path of the "timing bar" so as to directly provide the above mentioned trigger pulses in synchronism with desired points of either the displayed ECG or pressure traces.

The system of the present invention utilizes a transmitter coupled to appropriate electrodes for transmitting electrocardiogram (ECG) signals from the patient to the monitor and control equipment by telemetry so that problems such as cumbersome wires and ground loops are eliminated. The telemetry system allows almost instantaneous recovery of synchronization after defibrillation with the electrodes connected to the patient.

The monitor and control equipment comprises a console having a receiver mounted therein which receives and decodes the telemetry signals and applies them to trigger circuits which are adapted to reject the normal sources of low frequency interference such as movement and neuromuscular artifacts as well as high frequency electrical noise. Automatic gain control within the trigger circuits automatically compensates for varying ECG amplitudes thereby eliminating the need for frequent manual adjustment of the trigger threshold. The resulting R-wave trigger generated by the trigger circuits serves to activate the CRT sweep circuits so that the peak of the R-wave always appears at the left of the display screen. The analog ECG signal undergoes analog-to-digital conversion with the digital data at each sampling interval being stored in succeeding stages of a recirculating memory. The digital data appearing at the output of the recirculating memory undergoes digital-to-analog conversion and functions as an unblanking signal to the CRT control grid as well as controlling electron beam intensity to thereby display the ECG trace.

Electronics circuits are provided for the pressure channels and the analog signals developed similarly undergo an analogue to digital [A/D] conversion, transfer into recirculating memories and subsequent digital to analogue (D/A) conversion for selectively blanking and unblanking the electron beam in a multiplex manner to create pressure displays upon the CRT screen.

The CRT develops a "timing bar" which sweeps across the screen in synchronism with the ECG trace when the system is operated in the synchronized mode and which sweeps across the screen at a manually adjustable rate when operating in the unsynchronized mode. A cover plate is positioned across the bottom portion of the screen and is provided with a pair of elongated slots which are aligned parallel to the path of movement of the "timing bar". A pair of optical pickups are slidably mounted within a first one of the slots and are optically connected to remote mounted photodetectors by means of separate fiber optic bundles to activate the photodetectors as the "timing bar" passes its associated optical pickup. A similar optical pickup is mounted within the remaining elongated slot and is optically connected to a photodetector which develops an output signal when the timing bar passes its associated optical pickup. The optical pickups within the first elongated slot may be positioned at any desired location therealong so as to respectively initiate and terminate machine systole in accordance with desired positions along the ECG trace or, alternatively, in accordance with desired positions along a pressure trace such as an arterial pressure trace.

The photocell pickup which is slidably mounted within the second elongated slot may likewise be positioned with reference to any point along the ECG trace to develop an electrical pacing signal at any desired position of the ECG trace. The photocells, coupled to the pickups within the first elongated slot, develop signals for applying positive and negative pulsatile pressures to either the intra-aortic balloon, the Anstadt cup or the bypass pump for assisting and augmenting or for artificially performing the functioning of the patient's heart.

The pacing photocell develops an electrical signal to either fixed-rate pace a slow-rate or arrested heart or, alternatively, to provide for "paired pacing" in which the electrical pacing signal is used either exclusively or in conjunction with one of the mechanical assistance devices to cause the myocardium to revert to an additional refractory period due to the presence of the delayed pacemaker pulse applied to the heart a predetermined time period after selective ones of the R-waves so as to prevent the heart from responding to the next atrial P-wave before it is again repolarized. This technique is employed, for example, for reducing both the myocardium and assist rate to reduce the artial P-wave frequency by one half so as to correct for an excessive heart rate.

The photodetectors employed for controlling machine systole and diastole are applied to logic circuits which develop a solenoid trace on the CRT screen as well as providing for activation of the pressure and vacuum solenoids and for the care of the intra-aortic balloon, at either normal, halfnormal or one-quarter normal rates with the less-than-normal rates being utilized for patient weaning.

The pacing photodetector is coupled to a monostable multivibrator for developing constant width pulses utilized to "blank" the trigger circuits and to apply a "floating" signal to the heart for either pacing or paired pacing operation.

The CRT controls include a position control capability for positioning any of the displayed traces at any desired vertical location on the screen and even permit the traces to be superimposed for comparison purposes.

Circuitry is provided to temporarily "freeze" all traces, and to permanently "freeze" one of the traces at half the intensity of the remaining traces displayed on the screen to facilitate differentiation between the permanently "frozen" trace and the remaining traces.

The utilization of fiber optic bundles between the optical pickups and the photodetectors serves to completely isolate the photodetectors from spurious light signals as well as ionizing radiation enabling the photodetectors to be uniquely triggered by low light intensities from the CRT screen "timing bar" while making the photodetectors relatively immune from erroneous triggering by ambient light.

BRIEF DESCRIPTION OF THE FIGURES AND OBJECTS OF THE INVENTION

It is therefore one object of the present invention to provide a novel monitor and control system especially adapted for use in treating cardiac patients in which trigger signals for controlling mechanical and/or electrical assistive devices are taken directly from the display screen thereby eliminating "human" interfacing between display and control equipment.

Another object of the present invention is to provide novel control and monitoring equipment including display means for displaying real time and "frozen" patient cardiac data at different discrete intensities to significantly facilitate observation thereof.

Another object of the invention is to provide display equipment capable of simultaneously displaying a plurality of traces on a CRT face representative of patient data and of moving said traces to any desired position on the CRT face to facilitate evaluation of the patient data.

Still another object of the present invention is to provide novel monitor and control equipment for the treatment of cardiac patients and which has a capability of developing electrical pacing signals directly from the monitor display device for providing paired pacing and for eliminating synchronization.

Still another object of the present invention is to provide novel monitor and control equipment for use in the treatment of cardiac patients in which the control settings for non-actuated mechanical devices have no effect upon system operation.

Still another object of the present invention is to provide novel monitor and control equipment for use in treating cardiac patients in which signals for controlling the systole and diastole phases of mechanical assistive devices are triggered directly from the patient data appearing on a CRT display and which may be simply and directly adjustable so as to occur at operator selectable points of the displayed traces.

The above as well as other objects of the present invention will become apparent when reading the accompanying description and drawings in which:

FIG. 1 is a perspective view of the electronic synchronizer monitor system console and transmitter which embody the principles of the present invention.

FIG. 1a shows a top plan view of the console controls of FIG. 1.

FIG. 1b shows an enlarged perspective view of the CRT display mounted upon the console of FIG. 1.

FIG. 1c shows a simplified block diagram of a balloon adapter for use with the synchronizer-monitor system of FIG. 1.

FIG. 2 shows a sectional view of an intra-aortic balloon employed with the synchronizer-monitor system of FIG. 1 and the balloon adapter of FIG. 1c.

FIG. 3 shows a sectional elevational view of a bypass pump utilized with the synchronizer-monitor system of FIG. 1.

FIG. 4 shows a simplified block diagram of the pneumatic drive system provided as part of the synchronizer-monitor system of FIG. 1.

FIG. 5 shows a simplified block diagram of the system electronics employed for converting, storing and displaying patient ECG data.

FIG. 6a shows a simplified block diagram of the circulating memories and associated peripheral circuits utilized therewith for the purpose of storing and circulating ECG pressure and inflation-deflation data.

FIG. 6b shows the circuitry employed for controlling the contrast of the data displayed by the CRT.

FIG. 8 is a simplified block diagram showing the control circuitry for controlling the display of stored data.

FIG. 9b shows a simplified block diagram of the overall system electronics for operating the CRT display and for triggering the various assist devices.

FIGS. 10, 11a and 11b are plots showing waveforms useful in describing various operating modes of the system of the present invention.

FIG. 12 is a sectional view of a ventrical assistance cup

DETAILED DESCRIPTION OF THE INVENTION

Figure 7:
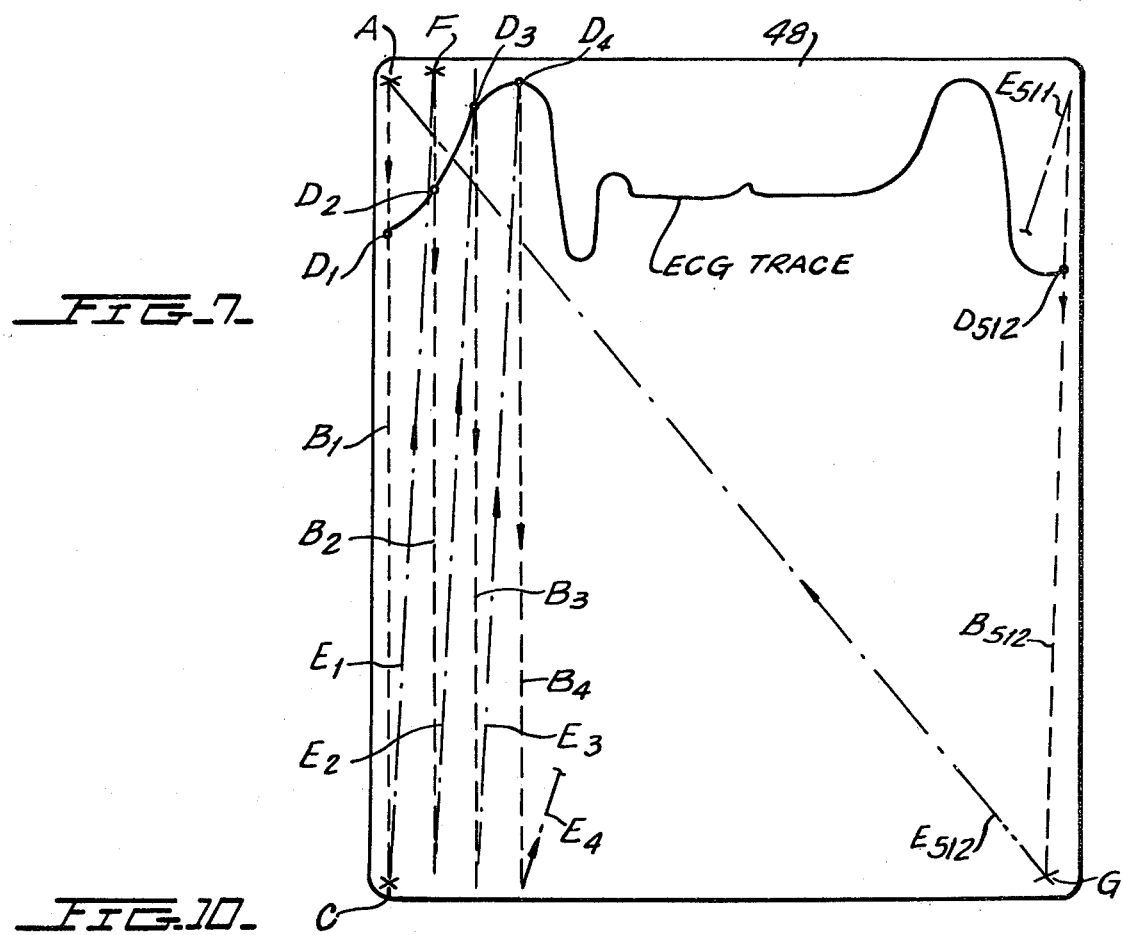
FIG. 7 shows a diagram useful in describing the manner in which data is displayed upon the CRT face.

FIG. 1 shows a system 10 embodying the principles of the present invention and being comprised of a compact transmitter 11 and a console 12 embodying the receiver monitor and control equipment, as will be more fully described.

Transmitter 11 is provided with electrical inputs 11a connected through leads 11b which in turn are coupled to electrodes positioned at appropriate locations either on or within the body of the patient being treated. In order that the transmitter 11 be as unobtrusive as possible, the transmitting antenna 11c is preferably taped as shown in 11d along one side wall of the transmitter casing, so as not to interfere with other equipment and/or numerous activities taking place in the vicinity of the patient, the transmitter preferably being positioned in relatively close proximity to the patient. The transmitter transmits pulse modulated type ECG data to a receiver facility housed within console 12 which may, for example, be located at some distance from the patient's bedside and is usually placed at a distance typically of the order of 5–15 feet. However, the precise separation distance between transmitter and receiver facility is not critical and greater or lesser separation distances may be utilized. Console 12 is provided with a receiver antenna 13 coupled to a receiver (not shown) housed within console 12. The console, which may be substantially freely wheeled to any appropriate position within the region or room in which the patient is located, is mounted upon casters 12a to facilitate such movement. Console 12 is powered by conventional line voltage, i.e., 120 volts a.c., and also includes a battery pack, not shown for purposes of simplicity, contained within the console and capable of operating the console electronics and compressor (to be more fully described), for up to one hour of portable operation. When the machine is operating from line voltage, one switch of the power pack is operated to the "battery power ON" position and the machine will continue to operate on battery power. The portable power pack has a built-in charger to automatically maintain the operable charge level. The charger circuit is of a low amperage type to guard against detrimental gas emissions from the lead-type batteries employed therein. A meter 13 on the front of the unit indicates battery conditions. Center scale reading on the meter indicates roughly halfcharged batteries, while a zero reading indicates that the batteries are exhausted (when operating on batter power).

Transmitter 11 has an operating frequency of 27 mHz and is of the citizens band crystal control type. The transmitter is of the pulsed modulator type and is battery operated with the battery pack capable of providing 50 or more hours of continuous operation. The inputs 11a are typically four in number and may be respectively connected to common, negative, positive, and Anstadt cup electrodes.

The console 12 has a compressor ON-OFF switch 14 and meter 14a providing an elapsed time reading for the compressor. One side wall of console 12 is provided with output tube 15 for connecting negative and positive pulsatile pressure output from the compressor system to the desired mechanical assistive device (i.e., Anstadt cup, bypass pump, or intra-aortic balloon). Connector 15 provides for electrical connection between the balloon monitoring electronics which provide alarms in the event of faulty mechanical operation.

The console is further comprised of adjustable knobs 16a and 17a which provide for manual manipulation and adjustment of the pulsed positive and negative pressures developed by the compressor unit, with meters 16b and (see FIG. 1) providing the readings therefor. Meter 13a provides an output reading for the continuous negative pressure at 18a for use, for example, with the Anstadt cup which typically is maintained at a pressure valve automatically controlled by the system pneumatics to a value which is always 25 mmHg below whatever the pulse vacuum value is set at.

Bottle 18 serves as a liquid trap means and has an output 18a for being coupled to the sustained suction tube of the Anstadt cup, for example. Bottle 18 is mounted upon the shelf of a rectangular-shaped opening provided on the left side wall of console 12, as shown in FIG. 1.

FIG. 1a shows the top control panel of console 12 in greater detail, which, in addition to the control knob and meters described hereinabove, further includes an automatic gain control knob 19 for adjusting the automatic gain control (AGC) of the receiver housed in console 12. The AGC meter 20 provides a visual reading of the automatic gain control setting.

Control knob 21 is manually adjustable to provide for the rate adjustment in beats per second of the "timing bar" sweep when the console is operating in the unsynchronized or "fixed rate" mode, or for limiting the maximum beats per second when operating in the synchronized mode, which operating modes will be more fully described hereinbelow.

Manually operable control knob 22 provides for the current magnitude setting of the pacer pulses developed by the console electronics. Terminals 23 are provided for attachment to a pair of leads (not shown for purposes of simplicity) which are coupled to the electrodes embedded within the patient for applying pacer pulses to the heart. Pushbuttons 24, 25, and 26 are utilized in a patient "weaning" mode of operation or operating at normal, one-half-normal, and one-quarter-normal repetition rates, which weaning technique will be more fully described hereinbelow.

Pushbuttons 27-30 are manually operable to control the intra-arotic balloon and Anstadt cup in either the synchronized or unsynchronized mode of operation. With respect to the pushbuttons 27-30, as well as pushbuttons 24-26, only that pushbutton which is depressed will become illuminated, indicating its selection. Pushbuttons 27 and 28 are utilized in the ECG triggered mode, while pushbuttons 29 and 30 are utilized in the unsynchronized mode. Pushbuttons 27 and 28 respectively condition the console electronics to cause the intra-aortic balloon and the Anstadt cup to be triggered by the ECG trace. Pushbuttons 29 and 30 respectively condition the console electronics to activate the Anstadt cup and intraaortic balloons in the unsynchronized modes. Toggle switch 31 is utilized to enable the Anstadt cup or bypass pump to be inflated at any time such that when toggle switch 31 is moved in the direction of arrow 31a the cup or pump will be deflated and when the toggle switch is moved in the direction of arrow 31b the cup will be inflated in accordance with the operating mode selected by pushbutton 27 or 30. The switches which are not depressed are decoupled from the console electronics so that any control settings of controls associated with the unoperated switches have no effect on the controls presently in operation.

The power ON-OFF toggle switch 32 turns the console either on or off. Pilot light 33 becomes illuminated when the power toggle switch 32 is in the ON position.

Pilot light 34 becomes illuminated when no trigger pulse is present. In those trigger pulse conditions, as will be described hereinbelow in greater detail, it may, for example, occur that the transmitter has not been electrically connected or has been accidentally disconnected from the ECG electrode embedded within the patient. In such instances pilot light 34 will be illuminated after a preset delay and the unit will automatically create an artificial trigger pulse as will be more fully described.

Electrical connector 35 is utilized to connect a first pressure transducer to the console electronics for coupling an analog pressure reading to the console for display purposes. A second connector 36 is provided for electrically coupling a second pressure transducer device to couple the second pressure reading to the console for display purposes.

Manually adjustable multi-turn adjustable potentiometers 37 and 38 associated with connector 35 are utilized to adjust the size and balance of the pressure signals coupled to the console through connector 35. Similar size and balance multi-turn potentiometers 39 and 40 are utilized to adjust the size and balance of a pressure trace for the pressure signal coupled to connector 36 of the console. Potentiometers 37 and 39 are utilized for adjust the peak-to-peak height of the first and second pressure traces, respectively, while potentiometers 38 and 40 serve to adjust the pressure traces relative to a pair of zero reference lines.

Manually operable control knob 41 operates a two-position rotary switch means for adjusting the sweep of the CRT display to either 0.25 or 0.5 seconds per grid line division on the CRT display face.

Two-position toggle switch 42 functions to place the CRT display in either the REPEAT or HOLD operating modes. When the toggle switch 42 is moved in the direction of arrow 42a toward the REPEAT position, the displays on the CRT are continually updated by the patient data signals derived from the electrodes coupled to the patient. When toggle switch 42 is moved in the direction shown by arrow 42b toward the HOLD position, the console electronics function to permit each of the traces being developed to complete one sweep and then freezes the trace being displayed and terminates the receipt of further analog information from the patient enabling the machine operator to store the patient data as of the last known sweep which was in progress when the toggle switch is moved to the HOLD position. The operator then depresses one of the pushbuttoms 43, 44, or 45 for transferring into the permanent memory that trace which is desired to be "frozen" on the CRT screen. The pushbottons 43, 44, and 45 respectively freeze the ECG, first pressure or second pressure traces and are selectively operated after manipulation of toggle switch 42 to the HOLD position. Pilot lamps 46, 47, and 48 selectively become illuminated dependent upon which one of the three pushbuttons 43-45 is depressed to indicate which one of the three analog signals has been "frozen", i.e., transferred to permanent memory.

FIG. 1 shows the console as being further provided with a housing 46 positioned above the top of console 12. A collar 47a is mounted upon the top surface of console 12. Elongated hollow cylindrical member 47b extends upwardly through collar 47a and into a collar 47c extending downwardly from the underside of housing 46. Electrical connections between console 12 and housing 46 extend through collars 47a and 47c and hollow cylindrical member 47b. The nature of the mechanical mounting for housing 46 enables rotation of housing 46 through a full 360° revolution to facilitate observation of the CRT screen 48 arranged immediately behind the rectangular frame 46a which defines the front opening in housing 46.

Making reference to FIG. 1b, one side wall of housing 46 is provided with manually operable control knobs 49-53, which are respectively associated with the balloon or solenoid, ECG, first pressure, second pressure, and permanent memory traces for moving each of these respective traces to any vertical position on the CRT display screen 48, as will be more fully described. Adjustment members 54, 55, 56, and 57, which constitute screw-type heads adjustable by means of a screwdriver type tool, enable adjustment in the vertical direction of the horizontal reference lines 58, 59, 60, and 61, which are arranged on the CRT display screen and associated with the first and second pressure traces. These reference lines may be adjusted to represent the minimum and maximum pressure values of the first and second pressure traces.

The CRT display screen shows display traces 62, 63, 64 and 65 which respectively represent ECG, balloon inflation, first pressure before augmentation and first pressure with assist display traces. The ECG trace is derived by telemetry from transmitter 11 (see FIG. 1) while traces 64 and 65 are derived from the pressure transducer (not shown) connected to console connectors 35 or 36. The balloon or cup solenoid inflation-deflation trace is derived from the console electronics which actuates either the intra-aortic balloon or Anstadt cup. This trace coincides with the physical positions of the optical pickup to be described hereinbelow.

The lower portions of the CRT display screen 48 are covered by a shield 66 which is provided with first and second horizontally aligned spaced, substantially parallel, elongated slots 67 and 68 which are aligned with the path of movement of a "timing bar" (to be more fully described), generated by the cathode ray tube within housing 46. A pair of optical pickups 69 and 70 are slidably mounted within slot 67 and are arranged to optically connect the optical pickups through fiber optic bundles 69a and 69b to photodetectors (not shown for purposes of simplicity) mounted within housing 46 for activating these photodetectors in a manner to be more fully described.

Elongated slot 68 has slidably mounted therein a third optical pickup 71, which likewise may be moved anywhere along slot 68 and is designed to optically couple the presence of a "timing bar" to a third photocell (not shown for purposes of simplicity) mounted within housing 46, which optical connection is provided by way of the fiber optic bundle 71a in order to activate the photodetector optically connected thereto when the "timing bar" passes the position of optical pickup 71.

One embodiment of the Austadt cup (i.e., mechanical ventricular assistor) is described in detail in U.S. Pat. No. 3,587,567, patented June 28, 1971. The Anstalt cup described in the above mentioned U.S. Patent is shown in FIG. 12. The cup 400 is attached to the ventricles (left ventrical L.V. and right ventrical R.V.) of the heart and is retained in position by continuous suction applied at the apex of the cup through tube 401. Alternating positive and negative pressures applied through tube 402 enter between the rigid cup shell 403 and a flexible polyurethane diaphragm 404 to augment both the systolic ejection and the diastolic filling of the ventricles. Diaphragm 404 is sealed to the upper open end of cup shell 403 by an appropriate epoxy ring 405. At least one electrode is incorporated in the cup (for example, see electrodes 44, 47 and 48 shown in FIG. 3 of the above mentioned patent) so that the ECG may be monitored for synchronization and defibrillation is possible without removing the cup from the heart. Since there is no direct blood contact between the gas entering tube 402 and the blood, heparinization is unnecessary. In order to maintain the natural balance of pulmonary versus aortic pressures, adequate cup pressure must be provided to completely empty the left ventricle. Thus, the maximum pulmonary volume is limited and near-normal pulmonary pressures are maintained.

FIG. 2 shows an intra-aortic balloon 80 comprising an elongated, semi-rigid plastic tube 81 having a thin elongated, substantially cylindrical shaped, flexible member 82 surrounding tube 81 and defining the balloon which is selectively inflated and deflated by positive and negative pressure pulses. Suitable means are provided for air-tightly securing ends 82a and 82b to tube 81. The extreme tip 83 of tube 81 is fitted with a small metallic member 83a to facilitate location of the tip by means of X-rays, as will be more fully described.

The portion of the tube 81 within balloon 82 is provided at staggered intervals with a plurality of holes 81a to permit the passage of negative and positive pressure pulses therethrough. A slender flexible rod 84 is inserted within tube 81 and extends from tip 83 downwardly through a major portion of balloon 82.

An incision is made in the left femoral area of the patient and the tip 83 of the balloon is inserted into the femoral artery and is maneuverted to the desired position just beneath the aortic arch. A chest X-ray is taken for the purpose of confirming correct balloon emplacement. Once the balloon is properly positioned, it is coupled to the pressure line 15 of console 12 which applies positive and negative pulsatile pressure to tube 81 in order to inflate the balloon in a manner to help augment the coronary perfusion during the filling phase of the balloon. The normal venturi effect, associated with a gas rushing through a catheter, is reversed by nylon rod 84 which serves as an obstruction within the catheter in the balloon chamber, thereby causing the balloon to fill from the catheter end towards the heart in a manner to help coronary perfusion. Thus, if a positive pulsatile pressure is applied to tube 81, the gas under pressure enters into the interior region of balloon 82 and passes through the openings 81a which are provided between lower tip 84a of rod 84 and lower end 82a of balloon 82 without any obstruction so as to fill the lower portion of the balloon first. Rod 84 serves to obstruct the otherwise free passage of gas under pressure through the openings arranged between tip 84a and the upper end 82b of balloon 82, causing this region of the balloon to inflate in a delayed fashion. When negative pulsatile pressure is applied to tube 81, balloon 82 is pulled toward tube 81 to shrink the balloon diameter so as to be substantially equivalent to the diameter of tube 81. The time occurrence of the positive and negative pulsatile pressures applied to balloon 80 are controlled directly from the CRT display and may either be synchronized with the ECG trace or may be triggered by electronic circuitry of the console 12, in a manner to be more fully described hereinbelow.

FIG. 1c shows a simplified block diagram of the balloon adapter utilized in combination with the synchronizer-monitor system of FIG. 1 and the intra-aortic balloon of FIG. 2. The balloon adapter 300 is comprised of an inlet conduit 301 for connection to the outlet 15 of console 12 (FIG. 1) to receive alternating positive and negative pressure pulses for operating the intra-aortic balloon. Conduit 301 communicates with safety chamber 302 whose interior is divided into two portions isolated by means of a thin plastic diaphragm 303 for separating balloon actuating gas in chamber portion 302a from the assist console pulse pressure and vacuum air supply in chamber portion 302b. A silicone diaphragm 304 separates the air filled portion 302b from a water filled portion 302c of chamber 302 which constitutes the displacement limiting portion of the chamber. A rigid sleeve or shaft 304a may be reciprocally moved within conduit 301 either to the left or right as shown by double-headed arrow 304b as the regions between the right-hand wall of safety chamber 302 and the sleeve 304a and diaphragm 304 is accordingly filled with water introduced by calibrated syringe 305 or where the water is removed from region 302c by reverse operation of the calibrated syringe. In other words, the water introduced into region 302c, the lower the possible stroke volume of diaphragm 303 and hence of intra-aortic balloon 80 (FIG. 2).

The balloon is coupled to balloon adapter 300 by means of a conduit 306 communicating with gas filled chamber portion 302a by means of manual stopcock 307. Manual stopcock 307 further includes transducer means 307a electrically connected by lead 308 to the leak detector 309, improper timing detector 310 and automatic purge system 311 for purposes to be more fully described. A differential pressure transducer 312 is coupled through conduits 312a and 312b which communicate with conduit 301 and the balloon actuating gas chamber portion 302a for a purpose to be more fully described. The output of the differential pressure transducer is electrically coupled to circuits 309, 310 and 311 to perform functions to be more fully described hereinbelow.

A purge valve 313 having an inlet 313a for receiving either air, helium or $CO_2$ and having an outlet 313b for exhausting gases into the atmosphere, is coupled through conduit 314 to an electrically operated purge solenoid 315 which, in turn, is coupled to the stopcock 307 through conduit 316. Output 311c of automatic purge system circuit 311 operates purge solenoid 315 in a manner to be more fully described. Alarm circuit 318 receives a pressure gating signal through line 319 from console 12. This signal is also coupled to respective inputs 309a and 310a of circuits 309 and 310, respectively.

In operation, and during a purge cycle a precise volume of gas is loaded into the balloon actuating gas portion 302a of safety chamber 302. During purging, the manual stopcock valve 307 is switched from the balloon position to the purge position. Circuitry 311 then controls console 12 through its outputs 311d and 311e to operate solenoids 112 and 113 shown in FIG. 4, resulting in a positive air pressure that pushes the actuating gas through the purge solenoid 315 and purge valve 313 into the atmosphere through outlet 313b. This is followed by a suction or negative pressure phase which draws the actuating gas (i.e., air, helium or carbon dioxide) through inlet opening 313a and purge valve 313 and solenoid valve 315 (which is now open at this time) into the balloon actuating portion 302a of safety chamber 302. As soon as a precise volume of air has entered the safety chamber, as indicated by a preset differential pressure across diaphragm 303 and measured by differential pressure transducer 312, the output signal of transducer 312 is applied to input 311b of the automatic purge system 311 to cause purge solenoid 315 to close. A purging indicator (not shown) such as a lamp may be provided to indicate that balloon adapter 300 is in a purge cycle. The purge indicator is enabled when the is extinguished when the purge cycle is completed. As the stroke volume of the balloon is increased, equal volumes of water behind diaphragm 304 are removed with the calibrated syringe 305. Shaft 304a is free to slide within the safety chamber housing to allow diaphragm 303 to position iteself for each new stroke volume.

As pulsed, positive pressure appears at outlet 15 (see FIGS. 1 and 4) this pulsed positive pressure causes diaphragm 303 to move to the left thereby urging the balloon actuating gas in safety chamber portion 302a through manual two-position valve 307 (which is now in the balloon position) and through conduit 306 to inflate the intra-aortic balloon 80 attached thereto. The pulsed negative pressure draws membrane 303 to the right causing the balloon actuating gas in chamber portion 302a to be withdrawn from the intra-aortic balloon. An improper timing alarm condition results when, during the pressure cycle, the pressure on the air side of diaphragm 303 is equal to the pressure on the balloon actuating side of the diaphragm as compared with the air pressure being slightly higher than balloon pressure during normal operation. The output of differential pressure transducer 312 is applied to input 310b of improper timing detector 310 which, develops an actuate vacuum signal at output 310d when the balloon is being inflated (i.e., the position signal derived from transducer 307a and lead 308) and when the pressure gating signal applied to line 319 from console 12 indicates that a pressure pulse is being applied to the system.

Leak detector circuit 309 develops an output signal at 309d during the deflation phase of the balloon. The precise actuating gas volume is measured in the dimensionally stable safety chamber is compared to the varying balloon elasticity and surrounding blood pressure during a pressure phase. During leak detection (i.e., during a vacuum pulse) the balloon actuating gas pressure must be slightly higher than the air pressure on the other side of diaphragm 303. If this differential pressure is higher or lower (as detected by transducer 312) and if inputs 319 and 308 indicate that a vacuum phase is occurring, then a leak signal is developed at output 309d to immediately control console 12 to develop a vacuum condition. Both the improper timing detector 310 and leak detector 309 are provided with delay circuits for delaying generation of their output signals for a period of the order of 0.20 seconds to allow the system to stabilize after the onset of the corresponding pressure and vacuum phases (i.e., pneumatic delays).

In cases where the balloon should be inflated for periods in excess of 2 seconds, the pressure gating signal derived from console 12 is applied to input 318a of alarm 318, which, if this condition persists for greater than two seconds, develops an alarm signal at its output 318b to immediately initiate a vacuum operation. In the case of power failure, vent hole 301a will allow the air pressure to be dissipated and the balloon 80 (FIG. 2) to collapse.

Pulsatile bypass pump 85, shown in FIG. 3, constitutes still another mechanical assistive device which may be utilized with the console 12 of FIG. 1 and is designed so as to be essentially a model of the left side of the heart. The pulsatile bypass pump has both an atrium and a ventricle to provide the following functions:

(1) may be synchronized for diastolic or systolic augmentation;
(2) has a non-occlusive design for low hemolysis;
(3) provides for continuous venous return flow;
(4) provides demand operation (i.e., will pump out whatever venous return is available from the patient);
(5) has controllable venous return suction so that the pump may be operated at patient level;
(6) will automatically maintain minimum reservoir level, if desired, although a reservoir is not necessary; and
(7) has a stroke volume indicator which employs no electronics.

Referring to FIG. 3, the blood enters the atrial chamber 86 through tube 87 which is coupled to the venous return. Chamber 86 is separated from an air-filled portion in the atrium by a flexible polyurethane diaphragm 88 coupled to the venous control suction by tube 89. The ventricle chamber 90, positioned below the atrial chamber 86, is filled when blood passes through a flexible dual-flap mitral valve 91. Pneumatic pressure from the console 12 is transferred through a saline column 92 by tube 93 and exerts a force on a polyurethane membrane 94 which separates blood in ventricle chamber 90 from the saline solution to push the blood into the arterial line 95 through an aortic flap valve 96. Plunger arrangement 97 limits the transmembrane pressures in the ventricle chamber as the head 97a of plunger 97 approaches the constricted neck portion 98 provided at the lower end of the ventricle chamber 90.

When the pump, which will be described in more detail hereinbelow, operates at less than flow capacity (i.e., where flow capacity equals ventricle displacement x rate), the polyurethane diaphragm 88 separating the blood from the air in the atrial chamber is simply forced down by the higher air pressure above this diaphragm. This causes diaphragm 88 to move downwardly and seal the narrow opening 99 between atrium 86 and ventricle 90 and the pump thereby simply shuts off. By controlling the amount of suction in the air portion of the atrial chamber 86 the exact level of venous suction or equivalent height of this venous blood column can be precisely controlled. Thus, the pump will shut off either at minimum reservoir level in an open oxygenator or can be controlled to provide the equivalent of a patient pump elevation without the necessity of relying on gravity flow for venous return through a small venous cannula, which is connected to tube 87.

The pneumatic drive system 100 shown in FIG. 4 and which is contained within console 12 is adapted to provide alternating pulsed pressure and pulsed vacuum controlled by the monitor and display electronics to be described in detail hereinbelow. The pneumatic drive system 100 comprises a motor operated compressor 101 having positive and negative outlet couplings 101a and 101b, respectively. These couplings are connected by tubes 102 and 103 to pressure and vacuum regulators 104 and 105, respectively, which are adjustable from the console panel by means of the control knobs 16a and 17a with the settings of these regulators being facilitated by pressure and vacuum meters 16b and 17b, respectively, (see FIG. 1a). The outputs of the pressure and vacuum regulators are coupled through conduits 106 and 107 to reservoirs 108 and 109, respectively, in order to allow large volumes of air under pressure to reach the assist transducer (to be more fully described). Reservoirs 108 and 109 are coupled through conduits 110 and 111 to solenoid valves 112 and 113, respectively, which are actuated by an electronic programmer provided in console 12 and to be more fully described, so as to alternately apply pressure or vacuum pulses to the transducer and mechanical assistance device. Conduits 114 and 115 are coupled through a Y-connector 116 to apply the positive and negative pressure pulses to the mechanical assistance device connected to console 12. The upper end of Y-connector 116 coincides with the outlet opening 15 of console 12 as shown in FIG. 1.

A continuous suction is also available from the console for the attachment of the ventricular assistance cup described hereinabove, or alternatively for increasing the venous return flow of the bypass pump 85 shown in FIG. 3. Thus, the upper end 18a of conduit 117 coincides with the tubular connection 18a of liquid trap bottle 18 of FIG. 1 and shown in block diagram form in FIG. 4. Conduit 107 is provided with a "tee-connector" 118 for coupling a vacuum regulator 119 to conduit 107. The suction in conduit 117 is automatically maintained approximately 25 mmHg below the pulsed vacuum setting. When a continuous suction is desired, valve 410 is opened applying the suction in conduit 117 to reservoir 109. When a pulsed suction is to be applied, valve 410 is closed and the pulsed suction passed by vacuum regulator 105 is applied to reservoir 109. Pressure regulator 104 is mechanically coupled to control knob 16a with the mechanical connection being represented by dotted line 121. Similarly, vacuum regulator 109 is mechanically coupled to control knob 17a with the mechanical connection being represented by dotted line 120.

FIG. 5 shows a simplified block diagram 130 of the electronic circuitry provided within console 12 of FIG. 1 for producing the analog signals which develop the ECG trace.

Transmitter 11 (note also FIG. 1) has its inputs coupled to the electrodes implanted within or placed upon the body of the patient and which serves to transmit a pulse modulated 27 mHz carrier to the receiver antenna 13. The pulse modulated carrier is demodulated by demodulator circuit 130b to develop an analog signal of the ECG trace at output 130a. Output 130a is coupled to the input of an analog-to-digital (A/D) converter 131 having an analog-to-digital reset input 131a which receives a pulse from the console timing and synchronizing electronics (to be more fully described) to reset the analog-to-digital converter. Immediately after reset the analog signal applied to the input of converter 131 by demodulator 130b is converted to a 6 bit binary output representative of the analog level applied to input 131b of converter 131 immediately after application of a reset pulse to input line 131a. The 6 bit binary word representative of the instantaneous analog level of the ECG is applied to respective inputs of a scratch pad memory 132 having a capability of storing as many as 16 6-bit binary words. The location in scratch pad memory in which the binary word is inserted is controlled by the application of a write control pulse applied to input 132a as well as a 4-bit binary word applied to inputs 132b which directs the 6-bit binary word appearing at the output of A/D converter 131 into a particular location or address in memory 132.

A circulating memory 133 having 512 stages with each stage capable of storing a 6-bit binary word is continually recirculated by clock pulses derived from a clock pulse source (to be more fully described) which applies clock pulses to clock input 133a. Thus the 6-bit binary words stored in circulating memory 133, which is typically referred to as a dynamic shift register, are continually recirculated within the memory. Binary words previously stored in scratch pad memory 132 are transferred at precise time intervals by the application of read control pulses applied simultaneously to the read/write control line 132a of scratch pad memory 132 as well as the read/write control line 133b of dynamic shift register 133. Thus the control electronics of console 12 (to be more fully described hereinbelow) serves to transfer the 6-bit binary words temporarily stored in scratch pad memory 132 into the proper time slot in dynamic shift register 133.

The application of a write control pulse to line 133b serves to couple the 6-bit binary word appearing in the output stage of dynamic shift register 133 to a digital-to-analog converter 134 which converts the 6-bit binary word applied thereto by memory output terminals 133c into an analog level. The analog level appearing at output 134a is amplified by amplifier 135 and is applied to the circuitry of FIG. 6 (to be more fully described hereinbelow) for developing an ECG trace on the CRT screen 48 in a manner to be more fully described.

FIG. 7 shows the screen 48 of the CRT in an exaggerated fashion for purposes of understanding the operating mode of the CRT display. The CRT 180 (FIG. 6b) comprises an electron gun having a typical cathode, control grid, and horizontal and vertical deflection means for causing the electron beam to scan the CRT screen 48 to form a raster in a manner substantially similar to the conventional raster developed in home TV receivers. FIG. 7 shows the manner in which the electron beam scans the face of screen 48, whose interior face is provided with a suitable phosphor material which becomes illuminated at those points where the electron beam is permitted to strike the phosphor coating. The electron beam begins its trace of screen 48 at point A which represents the upper left-hand corner of screen 48. The vertical deflection coil causes the beam to be moved downwardly as shown by dotted line $B_1$ so that the beam moves from point A to point C which constitutes the lower left-hand corner of screen 48. Normally the beam is blanked by applying a voltage level to the CRT control grid which is more negative than the cathode of the CRT.

Let it be assumed that it is desired to have a dot appear at the point $D_1$ along first line trace $B_1$. This is accomplished by applying a voltage level to the CRT control grid which is more positive than the cathode, i.e., unblanking the beam and allowing the beam to strike the phosphor at location $D_1$ and thereby causing illumination of the screen at this point.

As soon as the beam reaches point C it is rapidly moved in substantially the upward vertical direction along phantom line $E_1$ to a point F in very close proximity to point A. During the time that the beam moves between points C and F by the CRT deflection coils, it is blanked so as to be prevented from writing any information upon screen 48. It should be noted that the spacing between dotted lines $B_1$, $B_2$, $B_3$, . . . and $B_{512}$ has been grossly exaggerated in order to facilitate an understanding of the manner in which the CRT screen 48 is scanned by the electron beam.

Once the electron beam moves to point F it is then deflected vertically downwardly along trace line $B_2$. A dot $D_2$ is formed along line $B_2$ by applying a pulse to the CRT control grid at the instant at which the beam is passing point $D_2$ and which elevates the level of the control grid so as to be more positive than the cathode, thereby allowing the electron beam to strike the phosphor on screen 48 to form dot $D_2$. The dots $D_1$, $D_2$, $D_3$, $D_4$, . . . $D_{512}$ collectively form an ECG trace on screen 48 as was mentioned hereinabove. The trace lines $B_1$ through $B_{512}$ are positioned in very close proximity to one another and this fact coupled with the "memory" capability of the eyes of the observer serves to create what appears to be a substantially continuous trace on the CRT screen 48. As soon as the electron beam reaches the bottom point G of trace line $B_{512}$, the CRT deflection coils serve to deflect the beam from point G back to starting point A as represented by line $E_{512}$. As soon as the electron beam returns to point A a second raster is formed in substantially the same manner as that described hereinabove. The electron beam scans CRT screen 48 sixty times per second with the refresh rate being sufficient to create a display trace upon the face of the screen without "flicker". As was mentioned hereinabove in connection with FIG. 5, dynamic shift register 133 is provided with 512 stages with each of these stages being dedicated to one of the trace lines $B_1$ through $B_{512}$, respectively. The dynamic shift register is circulated in synchronism with the sweep of screen 48 by the electron beam. The console electronics (to be more fully described hereinbelow) maintains a running count of each of the trace lines as they occur and serves to circulate dynamic shift register 133 in synchronism with the scanning rate of the electron beam. Counter means provided in the console synchronizing electronics, (to be more fully described hereinbelow), serves to read out at output terminals 133c the 6-bit binary word of that stage of dynamic shift register 133 which is associated with the trace line $B_n$ presently in progress to form a dot along that (imaginary) trace line to create the ECG trace. The pressure, balloon inflation and "timing bar" traces are created in a similar fashion. However, the "timing bar is constituted by a short "line" as opposed to a "dot".

FIG. 6a shows the circulating memories provided in console 12. The ECG memory 133, as was previously described, is loaded at the appropriate time by means of the scratch pad memory 132. Clock pulses are applied to line 150 to cause each of the 512 binary words stored in memory 133 to appear at the output stage in synchronism with the electron beam trace line presently in progress on the CRT screen 48 (see FIG. 7). Each binary word is applied to the A/D converter 134, is amplified at 135 (by means to be more fully described, and is applied to the CRT control grid to control the formation of a dot at the appropriate location along the line $B_n$ presently being traced by the electron beam. Additional dynamic shift registers 151, 152, 153 and 154 are also provided in console 12. All of these dynamic shift registers have 512 stages with each stage being associated with one of the trace lines $B_n$ referred to hereinabove.

Dynamic shift register 151 has a capability of storing one binary bit per stage and has its input coupled to a logic circuit which monitors the negative and positive pulsatile pressures applied to the mechanical assistance device presently being used in order to constantly monitor the inflation or deflation state of the mechanical assistance device. The signal level of the transducer is clocked into a storage location in scratch pad memory 132 and, when the precise stage of circulating memory 151 appears at loading input terminal 151a, the binary bit temporarily loaded into scratch pad memory 132 at a particular address location is transferred into the balloon inflate-deflate circulating memory 151.

Dynamic shift register 152 is utilized to store a pressure reading $P_1$ derived from a transducer 155 which monitors pressure, for example, in the aorta of the patient. The output of the pressure transducer is coupled to connector 35 on the console panel shown in FIG. 1a and is electrically connected to analog-to-digital converter 156 which functions in a manner similar to the analog-to-digital converter 131 described previously in connection with FIG. 5. The A/D converter 156, after receiving a reset pulse, converts the analog signal applied to its input into a 6-bit binary word which is then temporarily stored in scratch pad memory 132 at an appropriate address location. The 6-bit binary word is then loaded into dynamic shift register 152 at the precise moment at which the stage in which 6-bit binary words should be located appears at the input terminal of register 152. Clocking signals are applied to line 150 to clock the 6-bit binary word in each stage to the output terminals at the precise time at which the electron beam trace line associated with the word coupled to the output terminals is in progress, at which time the appropriate 6-bit binary word of the output of dynamic shift register 152 is applied to digital-to-analog converter 158 to develop an analog signal which is amplified at 159 and applied to the cathode ray tube control grid in a manner to be more fully described.

Dynamic shift register 153 is utilized to store 512 6-bit binary words representative of a second pressure reading developed by a pressure transducer 160 which monitors a patient being treated. The output of pressure transducer 160 is coupled to connector 36 on the front panel of console 12 as shown in FIG. 1a and is applied to analog-to-digital converter 161 which converts the analog signal present at its output to a 6-bit binary word immediately after having been reset. This 6-bit binary word is immediately loaded into an appropriate location in scratch pad memory 132 and is transferred into dynamic shift register 153 when the proper stage of the dynamic shift register in which the 6-bit binary word is to be loaded appears at the input terminals of the dynamic shift register. The clock signals applied to line 150 connect that stage of the dynamic shift register which is associated with the trace line upon screen 48 presently being traversed to apply this 6-bit binary word to D/A converter 162. Amplifier 163 amplifies the analog signal and applies it to the cathode ray tube through additional circuitry, to be more fully described.

Dynamic shift register 154 constitutes a permanent memory means utilized to provide a permanent trace upon the CRT screen 48.

Permanent memory 154 is a dynamic shift register having 512 stages with each stage being capable of storing a 6-bit binary word. The input terminals of the dynamic shift register are coupled to the outputs of OR gates 164a through 164f. Each OR gate has three inputs respectively coupled to an associated one of the outputs of $P_1$ circulating memory 152, $P_2$ circulating memory 153 and the ECG circulating memory 133. Dynamic shift register 154 is continuously cycled by the pulses applied to line 150 and in synchronism with registers 151, 152, 153 and 133. The output of dynamic shift register 154 is coupled through the digital-to-analog converter 165 and amplifier 166 to the CRT control grid for developing a trace on the screen 48, in a manner to be more fully described. Dynamic shift register 154 steps at the same rate at which the CRT screen is scanned and 6-bit binary words representative of the trace line presently being scanned by the electron means are successively outputted and applied to digital-to-analog converter 165.

Permanent memory 154 is utilized to substantially indefinitely freeze one of the $P_1$, $P_2$ or ECG traces on the face of the screen 48 especially for the purpose of storing a pressure or ECG trace which has occurred "prior to augmentation" in order to enable a simple and direct comparison to be made between pre- and post-augmentation patient data.

Selection of the trace to be frozen is accomplished by depressing one of the pushbuttons 43, 44 or 45 provided on the control panel as shown in FIG. 1a. The depressed pushbutton (as well as the other pushbuttons) is comprised of an electrical switch coupling a signal to decoder 168 which, dependent upon the pushbutton depressed, provides an enable pulse to one of the three memories 152, 153 or 133 to transfer the contents of the enabled recirculating memory into memory 154. Since memories 152, 153, 133 and 154 are all circulating in synchronism, the time at which any of the buttons 43 through 45 is depressed is immaterial. Although the outputs of recirculating memories 152, 153 and 133 are coupled through the OR gates 164a through 164f, only that memory which has received an enabling signal is caused to transfer its contents to the permanent memory 154.

FIG. 6b shows the electronics interface between the dynamic shift registers and the cathode ray tube (CRT) 180 for creating traces on the screen. Each vertical blanking pulse which, from a consideration of FIG. 7, is triggered at the time that the electron beam is at point C, for example, is applied to the vertical blanking input terminal 173a of a vertical ramp generator 173 which operates to develop a ramp at the same rate and of the same slope as the vertical deflection ramp generator 174 which is utilized to apply a ramp signal to the CRT vertical deflection means 175. Considering the waveform diagram for box 173, a vertical blanking signal is applied at time $t_1$ causing ramp generator 173 to reset and thereafter begin the generation of a ramp signal which is simultaneously applied to one input of each of a first set of comparators 171-1 through 171-4 and one input of each of a second set of comparators 172-1 through 172-5, the comparators being divided into "full intensity" and "half intensity" groups for a purpose to be more fully described. The remaining inputs of comparators 171-1 through 171-4 are coupled to the outputs of summing circuits 170-1 through 170-4. The comparator 172-1 also has a summing circuit 170-5 coupled to its remaining input. Each input arm 170a of the summing circuits 170-1 through 170-4 is respectively coupled to the output of amplifiers 159, 163, 135 and 167 (see FIG. 6a), each of which amplifiers serve to amplify the analog signals representative of the first and second pressure, ECG and solenoid signals respectively stored in the circulating memories 152, 153, 133 and 151.

The remaining arms 170b of each of the summing circuits 170-1 through 170-4 are respectively coupled to the slide arms 174a-1 through 174a-4 of potentiometers 174-1 through 174-4, respectively. Each of these potentiometers comprises a resistor element with end terminals connected across a DC power source represented by the terminals +VDC and -VDC connected in common across each of the resistive elements. Each potentiometer is further comprised of the slide arms 174a-1 through 174a-4 which are mechanically adjusted by means of the control knobs 49 through 52 arranged along one side wall of the CRT housing 46 (see FIG. 1b).

For example, considering comparator 171-3, the summing circuit 170-3 associated therewith has its arm 170a coupled to the output of amplifier 135, shown in FIG. 6a, while the remaining arm 170b is coupled to slide arm 174a-3. The sum of these analog levels is compared by comparator 171-3 against the instantaneous analog value of the vertical ramp generator 173, causing comparator 171-3 to develop an output only at the precise moment when the analog levels of the signals being compared are equal. It should be seen that each output of the digital-to-analog converter determines the height of the ECG waveform for the ECG trace presently being developed by the CRT electron beam. The signal summed therewith from potentiometer 174-3 serves as a means by which the trace may be shifted either vertically upward or downward on the CRT screen 48 so as to enable any relative positioning between and among the various traces as well as even permitting superimposition of traces, which feature is extremely advantageous for use in comparing pre- and post-augmentation data derived from the patient. Since the vertical ramp generator 173 operates in synchronism with the ramp generator operating the CRT vertical deflection means, its output is equal to the output of the vertical ramp generator operating the vertical deflection means at every given instant of time. Thus at the precise moment when the output of summing circuit 170-3 equals the instantaneous analog value of the ramp generator 173, comparator 171-3 generates an output pulse.

Comparators 171-1 through 171-4 each have their outputs coupled to the base electrode of an associated transistor $Q_1$ through $Q_4$. The collectors of $Q_1$–$Q_4$ are all coupled in common to one terminal of resistor $R_1$, with the common connection also being coupled to trigger input terminal 176a of monostable multivibrator 176. The opposite terminal of $R_1$ is coupled to a +5 volt source.

Transistors $Q_1$–$Q_4$ collectively form an OR gate for coupling the output appearing at its four input terminals (i.e., the base electrodes of $Q_1$–$Q_4$) to the trigger input terminal 176a. Monostable multivibrator 176 supplies its positive trigger output 176b and its complementary negative trigger output 176c, i.e., a negative going pulse, to the respective inputs of gates 177 and 178. When either of the inputs to gate 177 goes high, the inverted output is applied to transistor $Q_{10}$ causing $Q_{10}$ to turn off and thereby applying +15 volts DC to control grid 180a of the CRT 180. Simultaneous therewith, the negative going pulse developed by monostable multivibrator 176 causes the output of gate 178 to go high which causes transistor $Q_{11}$ to conduct and serves to drive the cathode 180b of CRT 180 more negative simultaneously with the control grid 180a being driven more positive so as to develop a spot on the screen 48 of relatively high illumination intensity.

Comparators 171-1, 171-2 and 171-4 function in a similar manner whereby the summing circuits apply to their comparators a composite voltage made up of the position control voltages derived from the adjustable pots 174-1 through 174-4 and the analog voltages converted from each digital signal stored in the appropriate circulating memories, so as to develop a signal which is passed through the OR gate comprised of transistor $Q_1$ through $Q_4$ to trigger the monostable multivibrator 176 to develop spots of high illumination intensity on screen 48. Adjustment of the vertical positioning of the trace is accomplished by manual manipulation of the knobs 49 through 52 arranged along the side wall of the CRT housing 46.

The second group of comparators 172-1 through 172-5 have their outputs applied to the base electrodes of transistors $Q_5$ through $Q_9$, whose collectors are all connected in common to sources through resistor $R_2$. A common collector connection is also coupled to the trigger input 182a of monostable multivibrator 182 which has its output 182b coupled to gate 178. When monostable multivibrator 182 is triggered at 182a, it develops a negative going pulse at 182b causing the output of gate 178 to go positive which, as was described hereinabove, causes $Q_{11}$ to conduct so as to apply a negative going level to the CRT cathode 180b. It should be noted that no positive going level is applied to the control grid 180a at this time. However, the negative level applied to cathode 180b is sufficient to unblank the electron beam in order to create a spot on the screen. However, the spot created will be of half the intensity of a spot created by any of the comparators 171-1 through 171-4 which, as was described hereinabove, serves to trigger the control grid 180a and cathode 180b simultaneously with positive and negative going levels, respectively, to create a high intensity beam whereas the outputs of comparators 172-1 through 172-5 only trigger cathode 180b with a negative going pulse while maintaining the control grid 180a at its quiescent level.

The comparators 172-1 through 172-5 function in the same manner as comparators 171-1 through 171-4 wherein the analog level applied to the upper input of each comparator 171-1 through 171-4 is compared against the instantaneous analog level applied to the lower input of each comparator by the vertical ramp generator 173. Each of the input arms 183-1 through 183-4 coupled to the upper inputs of comparators 172-2 through 172-5, are respectively coupled to one of the slide arms 184-2 through 184-5, which cooperate with their resistive elements 185-2 through 185-5 to apply a DC level to a respective comparator by means of adjustment of one of the screw head adjustment members 54 through 57. The remaining input of each of comparators 172-2 through 172-5 is coupled to the output of the vertical ramp generator 173. Manipulation of any of the screw head adjustment members 54 through 57 serves to position the horizontal line traces 58, 59, 60 and 61 at any desired vertical position upon screen 48 and usually for the purpose of representing voltage level in the case of an ECG trace or representing pressure level in the case of a pressure trace.

The remaining comparator 172-1 functions with the permanent memory 154 of FIG. 6a in order to display the "frozen" trace upon CRT screen 48 at "half intensity".

When one trace of patient data such as, for example, either an ECG or a pressure trace, is inputted into permanent memory 154, the analog level of each of the 512 words in permanent memory 154 are sequentially and repetitively applied to D/A converter 165 and are then applied to one arm 170a of summing circuit 170-5, while the other arm 170b is coupled to slide arm 184-1 which is adjusted by manually adjusting control knob 53 on the side of the CRT housing 46 to position the permanent memory trace at any desired vertical location on the face of screen 48.

The vertical lines 191 appearing on screen 48 (see FIG. 1b) are developed by application of a signal to one input of gate 187 whose output is coupled to one input of gate 178 through gate 188. When a negative going pulse is applied to the upper input of gate 187, its output goes negative causing the output of gate 188 to go negative and hence driving the output of gate 178 positive to cause conduction of $Q_{11}$ thereby driving the cathode 180b negative relative to control grid 180a so as to cause a vertical line of "half intensity" to be developed upon screen 48. The duration of the pulse applied to input 187a is equal to the time required for the electron beam to sweep one vertical trace line $B_n$ (see FIG. 7) and is obviously timed to occur at the appropriate trace line in progress.

Input 187b is adapted to receive a blanking pulse which causes the respective outputs of gate 187 to go negative and gate 188 to go positive thereby causing the output of gate 178 to go negative and thereby preventing the cathode electrode of the CRT from being driven negative. Simultaneously therewith the output of gate 189 goes negative to disable both monostable multivibrators 176 and 182 assuring that the electron beam is blanked during receipt of a blank pulse, which serves to blank screen 48 during the time that the trace is returning from the lower right-hand corner (point G) to the upper left-hand corner (Point A) of the screen 48 as shown in FIG. 7. By applying the blank signal to gate 187 as well as gate 189, the vertical lines 191 are also blanked during the horizontal blank period.

Input terminal 192 receives the sync bar video signal which is utilized to develop the "timing bar" created along the lower margin of screen 48 for the purpose of controlling systole and diastole of the mechanical assistance device being controlled by the console electronics. The pulse applied to input 192, as will be more fully described, is applied to one input of gate 177 and one input of gate 188 causing gates 177 and 178, respectively, to go low and high whereby transistors $Q_{10}$ and $Q_{11}$ are rendered respectively non-conductive and conductive to develop a "timing bar" of a few adjacent short line lengths along the lower margin of screen 48. The manner in which the timing of the "timing bar" sync pulse is controlled will be described hereinbelow.

The CRT display has the capability of creating a trace which appears to progressively develop across the screen moving from left to right as new patient data is being inputted into the display electronics. It should be noted that, as the new display is being created, only that portion which has been loaded into the appropriate dynamic shift register will be displayed and the patient data yet to be inserted into the dynamic shift register and which would occupy the remaining portion of the trace, is blanked by application of a trace enable pulse to enable input 176d of the monostable multivibrator 176 which serves to blank the screen when the position count of the position counter (to be more fully described) is greater than the count of the data bit counter (also to be more fully described).

FIG. 8 shows the electronic circuitry 200 utilized for synchronizing the scanning of the CRT with the storage of patient data in the circulating memories referred to hereinabove as well as the development of the "timing bar". The circuitry 200 is comprised of a high frequency clock 201. The output of clock 201 is applied to a multistage binary counter 202 whose final output is coupled to multi-stage position counter 203, which is capable of counting from 0 through 512.

Decoder circuitry 204 is coupled to selected stages of counter 202 for developing the signals S1, S2 and S3 which occur in sequential fashion. Each count pulse developed at the output of counter 202 and applied to the input of position counter 203 occurs in synchronism with each of the vertical traces $B_1$ through $B_{512}$ referred to hereinabove with regard to FIG. 7. While each of these pulses occurs during an associated one of the trace lines $B_n$, the Signals S1 through S3 each represent a non-overlapping portion (upper, middle and lower) of each trace line $B_n$.

Decoder 205 is coupled to one stage of counter 202 and generates the memory sync and vertical reset pulses at its outputs 205b and 205c, respectively, which pulses are utilized to control the circulation of 6-bit data words in the circulating memories and to create a vertical reset trigger for resetting the vertical ramp generators 173 and 174 which respectively control vertical deflection of the CRT electron beam and activate the comparator circuits 171-1 through 171-4 and 172-1 through 172-5.

These outputs are further inputted to the composite blanking circuitry 206 which serves to develop an output 206a coupled to input 187b of gate 187, shown in FIG. 6b, for assuring that the trace is blanked when any of the events such as vertical reset, horizontal reset, or sync bar blanking occur.

The output pulses of counter 202 serve to advance position counter 203 through a count of 512, and cause position counter 203 to be automatically reset to step through each succeeding count of 512. The output stages of position counter 203 are coupled to one set of inputs of comparator 209 whose second set of inputs are coupled to the output stages of data bit counter 208 which is likewise capable of stepping through a count of 512. The stepping rate of data bit counter 208 is controlled by the sample rate circuitry 207 which is adjusted by means of manually operable control knob 41 (see FIG. 1a) to control the display trace so as to generate a trace of either one-quarter second or one-half second time intervals spaced between the vertical time division lines 191 (see FIG. 1b).

When position counter 203 steps to a count of 512, an output pulse is developed to activate decoder 212 which generates a horizontal reset pulse to reset the horizontal ramp generator 220 (see FIG. 6b) in order to initiate a fresh trace. Position counter 203 can be seen to maintain a count representative of the vertical line $B_n$ presently in progress on screen 48 and also representative of the stage of each of the recirculating memories 152, 153, 133 and 154 (see FIG. 6a) which is coupled with its associated comparator 171-1 through 171-4 and 172-1 (see FIG. 6b).

Data bit counter 208 is triggered by sample rate circuit 207 which in turn receives a trigger from the trigger circuit 223 shown in FIG. 5 and which is adapted to develop a narrow positive going trigger pulse at or near the peak of each R-wave of the ECG which serves as a means for initiating the data bit counter 208. Obviously, it can be seen that the occurrence of an R-wave in the ECG signal is totally independent of the scanning of the CRT screen. The count of the data bit counter 208 is simultaneously applied to comparator 209 and the control logic 213. When the count of position counter 203, which is applied to the first set of inputs of comparator 209, is unequal to the count in data bit counter 208 and applied to the second set of comparator inputs, control logic 213 develops a write signal at output 132a and an address code at outputs 132b of a particular address in scratch pad memory 132 to temporarily store the digital representation of the analog voltage of the patient data (ECG, $P_1$, $P_2$ and solenoid inflate/deflate) into particular address locations in the scratch pad memory. Since data is entering at a much slower rate than the cycling rate of the recirculating memories, when the count in data bit counter 208 equals the count in position counter 203, output 209a of comparator 209 develops an "equal to" signal which is applied to control logic 213 for developing a read signal at output 213a and the address of the temporarily stored patient data in the scratch pad memory for read out and transferring of this data into the proper stage in the appropriate recirculating memory.

Whenever the count in data bit counter 208 is less than the count in position counter 203, output 209b of comparator 209 generates a "less than" signal which is applied to the trace enable input 176b of FIG. 6b for the purpose of blanking the trace and preventing any old information from the previous trace from being displayed upon the CRT screen 48.

Sync bar counter 210 is utilized together with position counter 203 and comparator 211 to develop the "timing bar". The output of sample rate circuit 207 is applied to sync bar counter 210 which is capable of generating a count from 0 to 512 and which has its output stages coupled to one set of inputs of comparator 211, whose opposite set of inputs is coupled to the output stages of position counter 203. Thus sync bar counter 210 has its count advanced upon the occurrence of each sample pulse and when the position counter 203 equals the count in sync bar counter 210 comparator 211 develops an "equal to" signal at its output 211a which is applied to gate 214, which gate is enabled when the $S_3$ signal is developed by decoder 204 (during the lower portion of each trace line B) to develop a sync bar video signal output at 214a which, as was described hereinabove, is applied to input 192 of FIG. 6b which activates both gates 177 and 178 to drive CRT control grid and cathode, respectively, more positive and more negative to develop a "timing bar" of high intensity along the lower portion of screen 48, i.e., the portion beneath the shield or cover 67 (see FIG. 1b) for the purpose of activating the optical pickup elements 69, 70 and 71, in a manner to be more fully described. The sync bar signal has a duration sufficient to cause 4–8 adjacent vertical traces to be formed on the screen.

Thus each "timing bar" begins at the left-hand end of screen 48 and beneath shield 67 upon the occurrence of each trigger pulse and sweeps across the screen at a rate determined by the sample rate. The bar resets to the left of the screen whenever a trigger pulse is generated.

The trigger circuit 223 (FIG. 5), as was described hereinabove, functions to develop a trigger pulse upon the occurrence of each R-wave. In certain applications wherein the patient's heart rate may be excessive, it is desired to prevent the mechanical assistance devices from being activated at such a high rate. In this instance, the output of trigger circuit 223 is further coupled to a maximum rate control circuit 228 which is further manually adjustable by manipulating the control knob 21 provided on the console control panels, shown in FIG. 1, so as to provide any desired beat per minute rate, typically between 50 and 150 beats per minute. If trigger pulses are applied to maximum rate circuit 228 at a rate slower than the maximum rate set, then all of the R-waves initiated trigger pulses are passed by circuit 228. However, if the trigger pulses are developed at a faster rate than the maximum rate set, circuit 228 limits the development of pulses to the maximum rate setting so as to prevent the mechanical assistance device from being inflated and deflated at a rate greater than that set by maximum rate circuit 228.

Figure 9A:
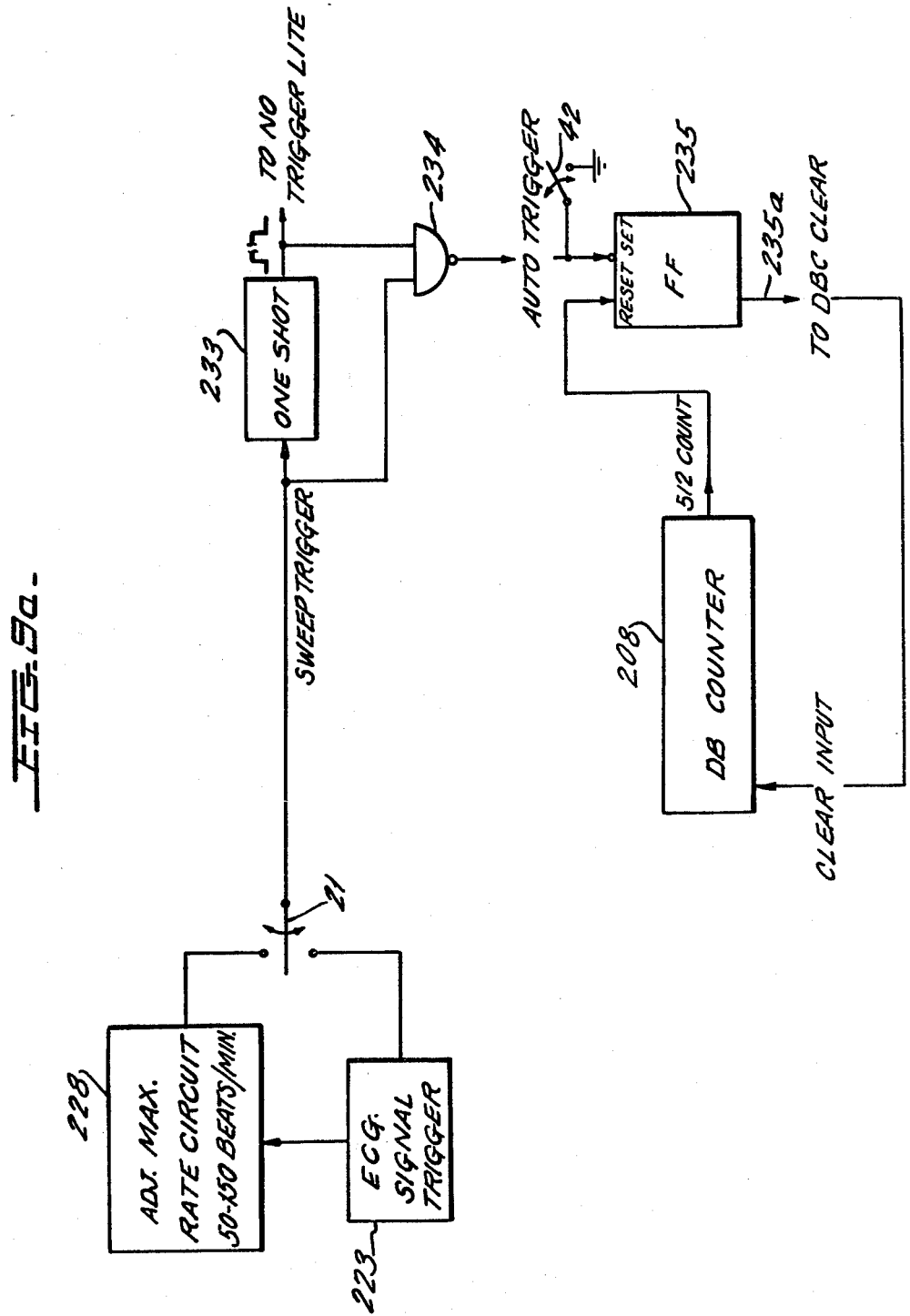
FIG. 9a is a block diagram showing the circuitry employed for operating the "trigger bar" display based upon either ECG or console generated triggering.

FIG. 9a shows the output of either the maximum rate circuit 228 or trigger circuit 223 as being coupled by switch means 21 to be simultaneously coupled to the trigger input of one-shot multivibrator 233 and one input of gate 234. The output of one-shot multivibrator 233 is coupled to the remaining input of gate 234 whose output is coupled to bistable flip-flop 235 which forms a part of sample rate circuit 207 of FIG. 8. The reset input of bistable flip-flop 235 is coupled to the last stage of data bit counter 208 and the output of 235a of bistable flip-flop 235 is coupled to the clear input terminal 208b of counter 208.

As each trigger pulse is passed by switch 21 it is applied to one-shot multivibrator 233 and to gate 234. Since the normal heart rate is usually at least of the order of 50 beats per minute the time spacing between successive R-waves is slightly more than one second and clearly less than 1.5 seconds. The occurrence of each R-wave triggers one-shot multivibrator 233 to generate a positive going output pulse which is reset 1.5 seconds after having been set. Thus, if R-waves are occurring at a rate of at least 50 beats per minute, one-shot multivibrator 233 is continually and repetitively reset before having an opportunity to time out. Thus, both inputs to gate 234 are simultaneously high causing a low output to be developed at the output of gate 234 to set bistable flip-flop 235. However, bistable flip-flop 235 cannot be read until it has been previously reset by a reset signal derived from data bit counter 208. A reset signal is developed only after data bit counter has stepped through a count of 512, each time the output of bistable flip-flop 235 clears the data bit counter 208 to initiate a new count.

In the event that the patient's heart stops or reduces to a rate below 50 beats per minute, or in the event that any of the ECG telemetry or electrodes are accidentally disconnected, one-shot multivibrator 233 will time out and its output will remain at a negative level causing a constant level to be maintained at the set input of bistable flip-flop 235. This allows the data bit counter 208 to continue to count after reaching the count of 512, which in turn, allows the patient's information to be displayed when there are no ECG trigger signals. The output of one-shot multivibrator 233 is also coupled to the NO TRIGGER lamp 34 provided on the console control panel, as shown in FIG. 1a. It should be noted that, in addition to the ECG trace disappearing from the screen, lamp 34 is illuminated to indicate a termination of receipt of ECG data.

As described above, toggle switch 42 functions to place the CRT display in either the REPEAT or HOLD operating modes. When toggle switch 42 is in the solid line position illustrated in FIG. 9a (the REPEAT position), flip-flop 235 is periodically set by the output of NAND gate 234 and the displays on the CRT are continuously updated by the patient data signal derived from the electrodes coupled to the patient. When toggle switch 42 is moved into the dotted line position illustrated in FIG. 9a (the HOLD position), the set input of flip-flop 235 is constantly low and the flip-flop 235 cannot be reset by DB counter 208. In this position, the console electronics function to permit each of the traces being developed to complete one sweep and then freezes the traces being displayed and terminates the receipt of further analogue information from the patient enabling the machine operator to store the patient data as of the last known sweep which was in progress when the toggle switch was moved to the HOLD position.

FIG. 9b shows a simplified block diagram of the console electronics which is useful for explaining the operation of the "timing bar" and synchronization of the mechanical assistance device presently being employed through the use of the photodetector pickup devices.

As was set forth hereinabove, receiver 130 applies the ECG analog wave to trigger circuitry 223 which, by means of switch 21 couples either the maximum fixed rate or the actual trigger circuit (i.e., R-wave) rate to horizontal deflection means 220 to apply a ramp signal to the CRT horizontal deflection means to begin a fresh trace on the CRT screen 48. The ECG information is applied to the CRT cathode and control grid in a manner described hereinabove during each vertical trace line to create the ECG trace. The pressure traces are created in a similar fashion.

The "timing bar" sweeps from left to right across the bottom portion of screen 48 and begins at the left-hand side of the screen upon the occurrence of each R-wave under control of a trigger pulse. The photodetectors 261 and 262 are connected to the optical pickups 69 and 70 through the fiber optic bundles 69a and 69b, respectively. As the "timing bar" passes pickup 69, photodetector 261 is activated to develop a pulse to set bistable flip-flop 263 initiating a positive going pulse which is applied to frequency divider circuit 264 adjustable by the pushbuttons 24, 25 or 26 provided on the control panel, as shown in FIG. 1a, to divide the output of bistable flip-flop 263 by either 1, 2 or 4. It should be noted that the weaning circuit is only active in the balloon mode. The outputs 264a and 264b of divider circuit 264 are coupled, respectively, to the pressure and vacuum solenoids 112 and 113, shown in FIG. 4, for applying positive and negative pulsatile pressure to the mechanical assistance device presently being controlled by the console electronics. Output 263a of bistable flip-flop 263 is coupled to the solenoid recirculating memory 151 to develop a display trace of the inflation and deflation state of the particular mechanical assistance device being utilized.

The point at which the mechanical assistance device initiates inflation and deflation may be chosen to correlate to any point along either the ECG trace or the pressure trace which is desired by the operator. To further facilitate this positioning, the ECG trace, if desired, may be moved vertically downward so as to be placed immediately above the slidable optical pickups in order to facilitate positioning of the start and stop systole pickups at the appropriate desired locations. Once adjusted, the "timing bar", when operating in the synchronized mode, initiates each trace upon the occurrence of the peak of each R-wave. The ECG trace typically displays three R-waves displaced in time. However, the "timing bar" is reset upon the occurrence of the peak of each R-wave and hence is utilized by the photocell pickup 69 and 70 to start and stop systole in synchronism with each and every R-wave. Divide-by-two pushbutton 25 and divide-by-four pushbutton 26 (FIG. 1a) when selectively depressed enables the sweep rate of the "timing bar" to be reduced by either one-half or one-quarter for "weaning" the patient.

Optical pickup 71 is optically coupled to photodetector 267 by fiber optics bundle 71a so that when the "timing bar" passes pickup 71, photodetector 267 is activated to trigger the monostable multivibrator 270 which develops a narrow pulse applied through transformer means 271 to an electrode embedded within the patient's heart for purposes of applying pacing signals to the patient. The output of monostable multivibrator 270 is also coupled to disable the synchronizer trigger circuits 223, whereby the console does not trigger on its own pacing signal. The output terminals 23 of transformer means 271 are shown as the pacer connection terminals provided at the center of the console control panel, shown in FIG. 1a, and these terminals may be connected to electrodes embedded within the patient's heart for defibrillation of the heart. Defibrillation occurs when operating in the unsynchronized mode wherein the heart is paced at a rate established by the console control panel for setting the maximum beats per minute control knob 21.

An extremely important technique for reducing the rate of beating heart and for achieving a lower rate of assistance is quite simply obtained by delaying the repolarization of the heart with a pacing pulse from the synchronizer equipment so that the heart will not respond to the next subsequent P-wave from the atria. In other words, the heart is maintained in its refractory phase (i.e., depolarized) longer than normal so that it will not respond to the next atrial P-wave before it is again repolarized. Thus, both the myocardium and mechanical assistance device are arranged to operate at half of the atrial P-wave frequency.

Paired pacing may be achieved with the use of either a unipolar or bipolar electrode inserted intravenously into the heart or by means of a small special point source electrode provided in the mechanical assistance cup. The synchronizer circuitry allows paired pacing and synchronization over the same electrode lead.

Figure 10:
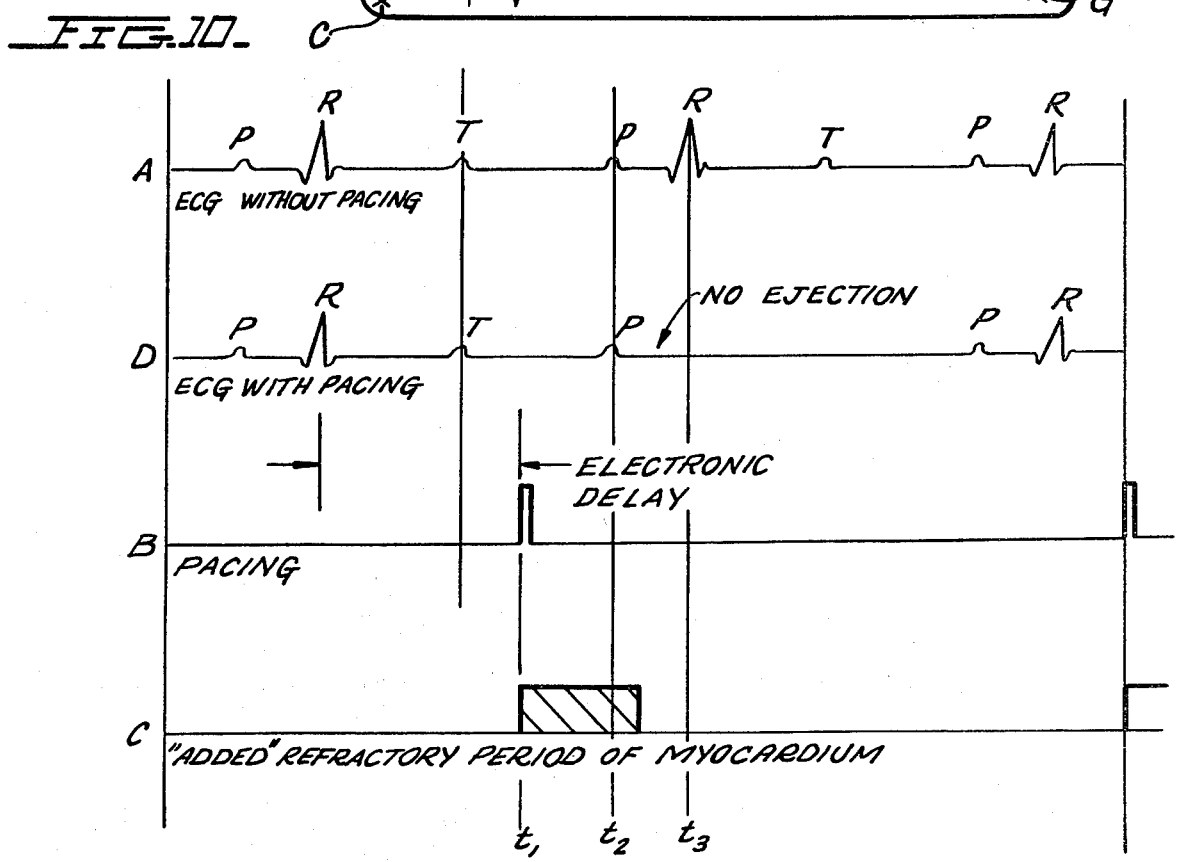

As shown in FIG. 10, the pacing electrodes are connected and with a current of about 5 mA of stimulation the pacemaker output is progressively delayed by adjustment of the optical pickup 71 until myocardial contraction only occurs on alternating P-waves. In case a synchronizer may respond to every P-wave (for example, if the pickup electrode is in the atria) the maximum rate control may be set half-way between the P-wave frequency and the ventricular contraction frequency to eliminate pacing on the P-wave with no ventricular contraction.

The waveforms of FIG. 10 show the manner in which paired pacing is accomplished wherein waveform A shows an ECG trace without pacing. Waveform B shows the pacing pulse developed by appropriate positioning of photocell pickup 71, which trace aids in comparative observation with the ECG trace represented by waveform A. Waveform C shows the "added" refractory period of myocardium which is developed by the pacing pulse so that the P-wave occurring at time $t_2$, and which is to activate the heart as shown by waveform A to create an R-wave trigger at time $t_3$, is ignored by the heart at time $t_2$ as shown by waveform D, whereby the myocardium fails to respond to develop the next R-wave which would otherwise occur at time $t_3$. Thus, by taking the benefit of display of the ECG trace A and moving the optical pickup 71 to a point related to the ECG trace to provide an electronic delay between the R-wave preceding time $t_1$ so that an additional refractory phase is added to the heart to reduce triggering of the heart to alternate P-waves and thereby cause the heart to beat at a rate one-half that of the beat rate which would otherwise occur without the use of paired pacing.

The overall operation of the synchronizer and display device is as follows:

Transmitter 11 is connected to the patient's electrodes for transmitting an ECG trace to the console which is turned on by operating the power ON/OFF switch 32. Assuming that the console is utilized to operate an intra-aortic balloon which is to be triggered by the ECG trace, pushbutton 27 is depressed. An ECG trace (and pressure traces, if desired) is displayed on the CRT screen 48. The trigger circuitry 223, in response to the ECG signal, triggers the reset and initiation of each "timing bar" which sweeps the screen at a rate controlled by the trigger pulses. The ECG display trace enables the operator to place the start and stop systole pickups at the proper locations in order to augment the beating of a weak heart. Let it be assumed that one pressure reading is being displayed on CRT screen 48, which pressure reading represents aortic pressure (for example) prior to balloon augmentation. In order to compare patient data prior to augmentation with patient data during augmentation, the Repeat/Hold toggle switch 42 is moved to the "Hold" position which couples the "set" input of flip-flop 235 (FIG. 9a) to ground potential to prevent trigger pulses from being applied to the data bit counter which thus stops operating when it reaches a count of "512". This decouples all subsequent patient data from being inputted into the recirculating memories as soon as the memories are filled. The memories thus fail to accept any further patient data and continue to recirculate their present contents. These display traces will thus be frozen on the CRT screen 48. Immediately thereafter, the operator may depress one of the pushbuttons 43, 44 or 45 representative of the trace which is to be permanently stored.

In the present example, the operator would depress the P1 button 44 causing the contents of the memory storing the P1 patient data to be transferred into the permanent memory 154. All other displays would then (temporarily) disappear from the screen 48 while the contents of the permanent memory is displayed on screen 48 at half-normal intensity. Pushbutton 44 need be depressed for only 1/30th of a second to assure transferrence of the entire contents of the P1 memory 152 (see FIG. 6a) into the permanent memory 154. Thereafter, toggle switch 42 is then moved to the "Repeat" position enabling all of the memories (with the exception of permanent memory 154) to receive updated patient data. The start and end systole pickups are then positioned in with the aid of the ECG trace in order to properly and significantly augment the beating of a weak heart. For example, in the use of an intra-aortic the left femoral artery, the balloon is normally inflated during diastole and is deflated during systole to decrease left ventricular pressure and heart work. Immediately after left ventricular ejection the balloon is again inflated to raise diastolic pressures and increase coronary perfusion. In accordance with the above, the R-waves should trigger balloon deflation. Electronically balloon deflation is delayed slightly so that the balloon deflation will coincide with the actual left ventricular ejection. Such delays are necessary since the R-wave precedes left ventricular ejection by about 0.07 seconds in humans. Immediately at the end of ejection, the balloon is again inflated and raises the diastolic pressure.

During balloon augmentation, the onset of balloon deflation (delay) and the duration of balloon deflation (systole duration) are adjusted in order to more effectively reduce left ventricular pressure and raise diastolic pressures during balloon inflation. For safety sake, the balloon should be deflated longer until optimum timing is established. If the machine systole duration is excessively long, the balloon is less effective since much of the cardiac output volume has dissipated and thereby is no longer available to improve coronary perfusion when the balloon inflates. The operator utilizes the ECG and pressure trace on the screen 48 to appropriately position the start and end systole optical pickups to assure proper and significant augmentation. The solenoid or "balloon" trace shows the direct result of pickup placement. The present pressure trace and the pre-augmentation trace (respectively displayed on the screen at full and half-intensity) can now be directly compared to easily determine the results of augmentation.

Augmentation through the use of the Anstadt cup is substantially similar in operation to that described hereinabove for the intra-aortic balloon except that pushbutton 28 is depressed.

For fixed rate operation of the intra-aortic balloon of Anstadt cup, pushbutton 39 or 29 is, respectively, depressed. The pressure traces prior to and during augmentation may be displayed in a similar manner to directly compare the results of augmentation when operating in this unsynchronized mode.

Paired pacing operation is utilized by coupling the patient's electrodes to the pacer terminals 23 provided on the console control panel (FIG. 1a) whereby the patient's ECG trace may be utilized to properly adjust for paired pacing.

After the patient's heart has been augmented, the heart becomes "lazy" and the patient must be gradually weaned from the balloon before augmentation is abruptly discontinued. Weaning consists of gradually making the balloon less effective, usually over a 24 to 36-hour period, by decreasing balloon volume in 10 cc increments and further by pumping at one-half or one-fourth of the patient rate. Weaning is continued as long as the patient shows no sign of regression (i.e., lower mean arterial pressure, decrease in urine output, elevated central venous pressure). Weaning is accomplished by operating one of the three pushbuttons 24 through 26 to reduce the balloon pumping rate to either one-half (pushbutton 25) or one-quarter (pushbutton 26) of the normal pumping rate.

FIGS. 11a and 11b are plots of waveforms useful in showing the augmentation resulting from use of the mechanical assistance devices described hereinabove in conjunction with the monitor and control equipment. As shown in FIG. 11a, an ECG waveform A is shown with arterial pressure waveforms B and C which, respectively, represent arterial pressure with no augmentation and with augmentation, i.e., with a cup on and operating.

In FIG. 11b, waveform A represents the ECG signal, waveform B represents arterial pressure prior to augmentation (i.e., balloon "Off"), waveform C represents arterial pressure as a result of augmentation (i.e., balloon "On" and pumping), waveform D represents the electronic delay between the R-wave trigger and balloon inflation imposed by the system electronics while waveform E represents the pneumatic delay imposed as a result of the physical coupling between the compressor and intra-aortic balloon whereby balloon deflation ultimately coincides with the actual left ventricular ejection.

For those applications in which it is desired to provide substantially instantaneous balloon inflation, i.e., coincident with the peak of each R-wave, the start systole optical pickup 69 is moved to the extreme left-hand end of slot 67. In this position the optical pickup closes switch arm 274a of a microswitch 274. While switch 274 is shown to the left of housing 46 for ease of illustration, it should be recognized that it is actually placed immediately adjacent the left-hand end of slot 67 whereby optical pickup 69 is in physical contact with switch 274 when pickup 69 is in position illustrated in FIG. 9b. Closed switch 274 couples the output of either trigger circuit 223 or maximum fixed rate circuit 228 directly to the set input terminal of bistable flip-flop 263 to provide instantaneous balloon deflation immediately upon the occurrence of either synchronized or unsynchronized trigger pulses.

It can thereby be seen that the foregoing invention provides novel monitor and control means for tracking and displaying patient data and, in conjunction therewith, for automatically, in the appropriate time sequence, operating mechanical assistance devices for augmenting the operation of a patient's heart. By tracking the patient's ECG or pressure readings, or both, triggering pulses are derived directly from the display thereby automatically operating the mechanical assistance devices. Any one of the traces may be permanently stored for comparing pre- and post-augmentation data, differentiation between traces may be distinguished by the full- and half-intensity levels of the stored and presently received patient data. The "timing bar" of the display, in addition to providing systole and diastole, also provides for the generation of pacing signals which, when operating in the unsynchronized mode, may be utilized to fixed-rate pace a heart. In the case of a beating heart, the pacing signals may be developed directly through the aid of the ECG display to provide an additional refractory phase thereby preventing the heart from reacting to every other P-wave so as to significantly reduce the beating rate of a heart having an excessive heart beat rate. The ability of moving any trace to any position on the CRT display face greatly facilitates observation and analysis of comparative pre- and post-augmentation patient data while at the same time being capable of accomplishing all of the above operating characteristics without the necessity for a complicated circuit design to accomplish all of the desired functions.

The employment of fiber optic bundles to couple the displayed "timing bars" to the photocells renders the photocells completely immune to ionizing radiation, such as X-radiation, for example, created by the CRT acceleration electrodes and further making the photocells substantially completely immune to ambient light while at the same time providing a simple, positive and direct technique for controlling the operation of assistance devices directly from the patient data displayed on the control monitor.

What is claimed is:

1. Display means for displaying at least two signals as traces on a display which contrast with one another to enhance the viewing thereof comprising:
    a cathode ray tube (CRT) having a display face, an electron beam generating means, a control grid and a cathode and first and second deflection means for deflecting an electron beam generated by said electron beam generating means;
    first and second ramp generating means for generating ramp signals and being respectively coupled to said first and second deflection means;
    clock means for resetting said first ramp generating means at a first predetermined rate;
    divider means coupled to said clock means for resetting said second ramp generating means at a second predetermined rate which is 1/nth said first rate;
    a plurality of comparator means at least equal in number to the number of signal traces adapted to be simultaneously displayed on said tube face, said comparator means having first and second inputs and an output for generating a signal when the signals at said first and second inputs are substantially equal;
    third ramp generating means operated by said clock means in synchronism with said first ramp generating means and being coupled to one input of each of said comparators;
    summing circuit means having first and second inputs and an output coupled to the remaining input of its associated comparator means;
    each signal to be displayed being coupled to one input of an associated one of said summing circuit means;
    adjustable signal level means for coupling an adjustable d.c. level to the second input of each of said summing circuit means whereby the signal at said first input controls the size and shape of said trace and wherein the d.c. level at said second input controls the position of the trace on the display face;
    means coupled between each of said comparator means and said cathode and control grid of said CRT and responsive to said signal at the output of said comparator means to render said control grid sufficiently positive relative to said cathode to unblank the CRT electron beam.

2. Means for displaying traces of different intensities on the face of a cathode ray tube (CRT) having an electron beam generating means including a cathode and a control grid, and means for deflecting the electron beam, said display means comprising:
    clock means operating at a predetermined repetition rate;
    means controlled by said clock means for operating said deflection means to cause said beam to scan said screen in a line by line fashion and repetitively refresh the line by line scan;
    first and second recirculating memory means each adapted to store data representing first and second traces to be displayed on said screen, said data comprising a plurality of data words and including means coupled to said clock means for circulating said data words in said memory at the same rate as said electron beam is caused to scan said screen;
    first circuit means having a first operating state for normally maintaining said control grid at a voltage to blank said electron beam and adapted to shift to a second operating state to simultaneously raise the voltage level on said control grid and lower the voltage level on said cathode to unblank said beam at a first intensity and having a third operating state for altering the voltage level on only a selected one of the cathode and the control grid to unblank said beam at a second intensity lower than said first intensity;
    each of said first and second memory means having an output stage;
    second circuit means responsive to the contents of said first recirculating memory means output to cause said first circuit means to trigger said second operating state a predetermined time during each line trace;
    third circuit means responsive to the contents in the output stage of said second recirculating memory means for triggering said first circuit means to said third operating state a second predetermined time during each line trace.

3. The device of claim 2 wherein said deflection means comprises first ramp generator means for reciprocally deflecting said electron beam in a first direction to move along the paths defined by the aforesaid lines;
    said second circuit means comprising first comparator means and responsive to the instantaneous value of the data word at the output of said first memory means and the instantaneous value of the output signal developed by said ramp generating means for triggering said first circuit means to said second operating state only when the levels of the inputs to said comparator means are equal.

4. The device of claim 3 wherein said third circuit means comprises second comparator means and responsive to the instantaneous value of the data word at the output of said second memory means and the instantaneous value of the output signal developed by said ramp generating means for triggering said first circuit means to said third operating state only when the levels of the inputs to said comparator means are equal.

5. The device of claim 3 wherein said second circuit means is further comprised of one-shot multivibrator means responsive to the output of said first comparator means for applying a trigger pulse of a preset time duration to said first circuit means.

6. The device of claim 4 wherein said third circuit means is further comprised of one-shot multivibrator means responsive to the output of said second comparator means for applying a trigger pulse of a preset time duration to said first circuit means.

7. Display means comprising:
a cathode ray tube having a display face, electron beam generting means and means for deflecting the electron beam developed by the electron beam generating means to scan across the display face a plurality of times;
recirculating memory means for storing binary coded words and having an input and an output;
means for shifting the binary coded words stored in said recirculating memory means at a rate substantially equal to the rate at which the electron beam scans across said display screen;
input means for receiving the signal to be displayed which is presented to said input means in analog form;
analog to digital converter means for converting the aforesaid signal presented to said input means into binary coded words at a sampling rate substantially equal to the rate at which binary coded words are shifted in said recirculating register;
scratch pad memory means;
means operated at a frequency rate equal to the shifting rate of said recirculating memory means for developing an identifying code to identify the order in time of each binary code word developed by said analog to digital converter at the aforesaid sampling rate;
said recirculating memory means including counting means for determining which stage of said recirclating memory means is coupled with said input;
means for transferring binary coded words to said scratch pad memory means when the identifying code of said binary coded word fails to coincide with the state of said counting means;
means for transferring the binary coded word previously transferred to said scratch pad memory means into said recirculating memory means through its said input when the identifying code of the binary coded words in said scratch pad memory means coincides with the state of said counting means;
means responsive to the coded data word at the output of said recirculating memory means for generating an unblanking pulse to cause said electron beam generating means to develop a dot during the line scan associated with the binary coded word which is presently coupled to the output of the recirculating memory means.

8. The display means of claim 7 further comprising means responsive to a particular portion of the aforesaid signal presented at said input means for generating an initiate display signal;
said means for generating an identifying code for each binary coded word comprising counter means for associating each binary coded word generated after the initiate display signal with a predetermined count wherein each count is increasingly greater than the last preceeding count;
means responsive to the last count developed by said counter means for preventing any binary coded words in stages of said recirculating memory means having a higher number than the last count developed by said counter means from developing an unblanking pulse whereby only newly developed signals are displayed on the screen of said display means.

9. Apparatus for displaying a signal comprising:
clock means;
first counter means having a predetermined number of stages for generating a plurality of signals each developed upon the occurrence of increasingly larger counts, each of said counts being less than the count capacity of said first counter means;
said first counter means further including means for generating a first reset signal when said first counter means reaches its capacity whereby said first counter means automatically resets to begin a new count;
a cathode ray tube display device including deflection means, electron beam generating means and beam unblanking means;
means responsive to each of said first reset signals developed by said first counter means for generating a first ramp signal applied to said first deflection means;
second counter means for counting said first reset signals and having a predetermined capacity and including a first set of outputs for generating a signal representative of the count at any given instant and a second reset output for generating a second reset signal when said second counting means has reached its capacity and is reset to begin a new count;
second ramp generating means responsive to each of said second reset signals of said second counter means for applying a second ramp signal to said second deflection means whereby each said second ramp signal applied to said second deflection means is automatically initiated after N of said first ramp signals have been applied to said first deflection means;
recirculating memory means for storing digital words and having an input, an output and a plurality of stages at least equal to the count capacity of said second counting means;
the input and output of said recirculating memory means being connected whereby digital words stored in the stages of said recirculating memory means are transferred from the output stage to the input stage for continuous recirculation;
analog to digital converter means for converting the signal to be displayed, which is presented to said analog to digital converter means in analog form, into digital words at a sampling rate equal to the repetition rate of said first ramp generating means;
means for identifying each digital word;
means for transferring ditital words to said recirculating memory means when the state of said identifying means coincides with the count of said second counter means;
means responsive to the digital word at the output of said recirculating memory means for causing the beam unblanking means to unblank said electron beam to generate a dot of said screen during the line scan being generated;

means responsive to selected ones of the plurality of signals generated by said first counting means and to a predetermined portion of said analog signal for operating said beam unblanking means to generate a timing bar which advances across the display screen at the same rate as the display developed under control of said recirculating memory means for use in controlling the occurrence of external operations in synchronism with the signal being displayed.

10. Display means comprising:

a cathode ray tube assembly having a display screen, electron beam generating means, electron beam control means for selectively unblanking the electron beam and first and second deflection means;

first means for generating a first deflection signal for driving said first deflection means to deflect the electron beam in a first line scan direction;

second means for generating a second deflection signal to deflect the electron beam in a second direction whereby one of said second deflection signals is generated during the generation of every group of N of said scan lines;

clock means generating clock signals for resetting said first means at a predetermined rate;

third means for receiving an analog signal to be displayed;

analog to digital converter means coupled to said third means and responsive to said clock means for sampling said analog signal at said predetermined rate to develop an output comprising a digital word representing the level of said analog signal at the time of said sampling;

first recirculating memory means having an input and output and at least N stages wherein each stage is adapted to store one of said digital words and wherein each digital word is associated with one of said scan lines;

the output of said first recirculating memory means being coupled to the input, said first recirculating memory means being coupled to said clock means for shifting the digital words through the stages of said first recirculating memory means at said predetermined rate and whereby the digital word at the output is shifted back into said input;

display control means coupled to said electron beam control means responsive to the digital word at the output of said first recirculating memory for unblanking the electron beam at a particular location along the scan line associated with the digital word at said output, said location being determined by the value of said digital word to develop a dot on said screen;

trigger means responsive to a predetermined portion of said analog signal for developing a trigger signal independently of said clock means;

means responsive to said trigger signal and said clock for assigning an identifying code to each digital word developed by said analog to digital converter means, each of said identifying codes being associated with one of said scan lines;

scratch pad memory means;

counting means for counting said clock pulses;

means for transferring a digital word to said scratch pad memory means when the count of said clock pulses in said counting means fails to compare with the identifying code of said digital words;

means for transferring the digital words stored in said scratch pad memory means to the input of said recirculating memory means when the count of said clock pulse compares with the identifying code of the digital word stored in said scratch pad memory means.

11. The display means of claim 10 wherein said analog signal comprises an electrocardiogram signal, said trigger means being adapted to generate a trigger signal upon the occurrence of the R-wave portion of said electrocardiogram signal.

12. The display means of claim 11 wherein said trigger means is responsive to the peak value of said R-wave portion to generate said trigger signal.

13. The display means of claim 10 further comprising second recirculating memory means similar to said first recirculating memory means and being coupled to said clock means for recirculating the contents thereof at said predetermined rate;

means responsive to a "freeze" request for transferring the contents of said first recirclating memory means to said second recirculating memory means;

second display control means responsive to the digital word at the output of said second recirculating memory means for causing said electron beam control means to unblank the electron beam at a particular location along the scan line presently being scanned by the electron beam the location along said scan line being determined by the value of said digital word at the output stage of said recirculating memory means to develop a dot on said screen.

14. The display means of claim 13 wherein said second display control means further comprises means for causing said electron beam control means to unblank said electron beam at a level different from said first display control means to cause the displays developed by the contents of said first and second recirculating memory means to be at different light intensities.

15. The display means of claim 10 further comprising means for resetting said first counting means responsive to a predetermined portion of said analog signal;

second counting means for counting clock pulses to simultaneously reset said first and second counting means when said second counting means has reached its capacity and has been reset;

means for preventing said electron beam control means from unblanking said electron beam when the count of said second counting means is greater than the count of said first counting means to prevent the display of incorrect data.

16. The display means of claim 15 wherein said second counting means is further responsive to a predetermined count of said first counting means and the next trigger signal to permit said first recirculating memory means to store a plurality of digital words substantially equal to the storage capacity of said first recirculating memory means to prevent resetting of said second counting means by each succeeding trigger signal.

17. Display means for displaying at least two signals as traces on a display which signals contrast with one another to enhance the viewing thereof, comprising:

a cathode ray tube assembly (CRT) having a display face, an electron beam generating means, a control grid and a cathode;

first and second deflection means associated with said CRT for deflecting an electron beam generated by said electron beam generating means;

first and second ramp generating means for generating ramp signals, said first ramp signal having first repetition rate said second ramp signal having a second repetition rate which is 1/Nth said first repetition rate, said first and second ramp signals being respectively coupled to said first and second deflection means for deflecting the electron beam in first and second mutually perpendicular directions;

first and second comparator means for each of the signal traces to be displayed on said tube face, each of said comparator means having first and second inputs and an output for generating a signal when the signals of said first and second inputs are substantially equal;

means responsive to said first ramp signal for developing a position signal representing the position of the electron beam as it sweeps a display face in said first direction, said position signal being coupled to one input of each of said comparators;

first and second summing circuits associated with said first and second comparators and having first and second inputs and an output coupled to the remaining input of its associated comparator means;

means for coupling each signal to be displayed to one input of an associated one of said summing circuits;

adjustable signal level means for coupling an adjustable DC level to the second input of each of said summing circuits whereby the signal of said first input controls the size and shape of said trace and wherein the DC level of said second input controls the position of the trace on the display face;

means coupled between the outputs of said first and second comparator means and said cathode and control grid and responsive to a signal at the output of said first comparator means to momentarily cause a voltage level of said control grid to increase and responsive to a signal at the output of said second comparator means to momentarily cause a voltage level of said control grid to increase and the voltage level at said cathode to decrease whereby the first and second traces are displayed at different intensities.

* * * * *